United States Patent
Jung et al.

(10) Patent No.: US 11,492,415 B2
(45) Date of Patent: Nov. 8, 2022

(54) ANTIBODY FC VARIANTS FOR INCREASED BLOOD HALF-LIFE

(71) Applicants: KOOKMIN UNIVERSITY INDUSTRY ACADEMY COOPERATION FOUNDATION, Seoul (KR); OSONG MEDICAL INNOVATION FOUNDATION, Chungcheongbuk-do (KR)

(72) Inventors: Sang Taek Jung, Gyeonggi-do (KR); Sanghwan Ko, Seoul (KR); Tae Gyu Lee, Seoul (KR); So Young Choi, Sejong-si (KR); Soo Han Lee, Seoul (KR); Myung Ho Sohn, Sejong-si (KR); Su Jin Kim, Chungcheongbuk-do (KR); So Ra Park, Chungcheongbuk-do (KR); Jong Shik Park, Sejong-si (KR); Ju Hyeon Lim, Sejong-si (KR)

(73) Assignees: KOOKMIN UNIVERSITY INDUSTRY ACADEMY, Seoul (KR); OSONG MEDICAL INNOVATION FOUNDATION, Chungcheongbuk-Do (KR)

( * ) Notice: Subject to any disclaimer, the term of this patent is extended or adjusted under 35 U.S.C. 154(b) by 182 days.

(21) Appl. No.: 16/603,273

(22) PCT Filed: Apr. 6, 2018

(86) PCT No.: PCT/KR2018/004104
§ 371 (c)(1),
(2) Date: Oct. 7, 2019

(87) PCT Pub. No.: WO2018/186717
PCT Pub. Date: Oct. 11, 2018

(65) Prior Publication Data
US 2020/0223938 A1   Jul. 16, 2020

(30) Foreign Application Priority Data

Apr. 7, 2017   (KR) .................. 10-2017-0045142
Apr. 13, 2017  (KR) .................. 10-2017-0047821
Apr. 13, 2017  (KR) .................. 10-2017-0047822

(51) Int. Cl.
C07K 16/00   (2006.01)
C07K 16/32   (2006.01)

(52) U.S. Cl.
CPC ........ *C07K 16/32* (2013.01); *C07K 2317/732* (2013.01); *C07K 2317/92* (2013.01); *C07K 2317/94* (2013.01)

(58) Field of Classification Search
CPC ............. C07K 16/32; C07K 2317/732; C07K 2317/94; C07K 2317/52; C07K 2317/72
See application file for complete search history.

(56) References Cited

U.S. PATENT DOCUMENTS

| 2007/0148164 A1* | 6/2007 | Farrington ............. A61P 43/00 424/133.1 |
| 2009/0041770 A1 | 2/2009 | Chamberlain et al. |
| 2012/0009188 A1* | 1/2012 | Behrens ................. A61P 11/06 424/133.1 |
| 2016/0244526 A1* | 8/2016 | Igawa ............... C07K 14/70535 |
| 2017/0029505 A1* | 2/2017 | Griffin ............... C07K 16/3015 |

FOREIGN PATENT DOCUMENTS

| KR | 10-1792191 | 10/2017 |
| KR | 10-1792205 | 10/2017 |
| WO | 2010/106180 | 9/2010 |
| WO | WO2015158867 | * 10/2015 |
| WO | 2016098357 | 6/2016 |

OTHER PUBLICATIONS

Monnet et al. (Frontiers in Immunology 6: 1-14, article 39, 2015) (Year: 2015).*
Ghetie et al., "Multiple Roles for the Major Histocompatibility Complex Class I-Related Receptor FCRN", Annu. Rev. Immunol. 2000, vol. 18, pp. 739-766.
Kohler et al., "Continuous Cultures of Fused Cells Secreting Antibody of Predefined Specificity", Nature, Aug. 7, 1975, vol. 256, pp. 495-497.
Deisenhofer, "Crystallographic Refinement and Atomic Models of a Human Fc Fragment and Its Complex with Fragment B of Protein A from *Staphylococcus areus* at 2.9- and 2.8-A Resolution", American Chemical Society, Apr. 28, 1981, vol. 20, No. 9, pp. 2361-2370.

(Continued)

*Primary Examiner* — Lei Yao
(74) *Attorney, Agent, or Firm* — Duane Morris LLP; Gregory M. Lefkowitz; Brandon A. Chan

(57) ABSTRACT

The present invention relates to a polypeptide including an Fc variant produced by substituting a portion of the amino acid sequence of the Fc domain of a human antibody with a different amino acid sequence. The present invention also relates to an antibody including the polypeptide. The Fc variant can find application in a wide range of antibodies and Fc-fusion constructs. In one aspect, the antibody or Fc fusion construct of the present invention is a therapeutic, diagnostic or laboratory reagent, preferably a therapeutic reagent. The Fc variant is suitable for use in the treatment of cancer because its in vivo half-life can be maximized by optimization of the portion of the amino acid sequence. The antibody or Fc fusion construct of the present invention is used to kill target cells that bear a target antigen, for example cancer cells. Alternatively, the antibody or Fc fusion construct of the present invention is used to block, antagonize or agonize a target antigen. For example, the antibody or Fc fusion construct of the present invention may be used to antagonize a cytokine or a cytokine receptor.

7 Claims, 33 Drawing Sheets
Specification includes a Sequence Listing.

(56) References Cited

OTHER PUBLICATIONS

Raghavan et al., "Fc Receptors and Their Interactions With Immunoglobulins", Annu. Rev. Cell. Dev. Biol., 1996, vol. 12, No. 181, pp. 181-220.

Monnet et al., :Selection of IgG Variants With Increased FcRn Binding Using Random and Directed Mutagenesis: Impact on Effector Functions, Frontiers in Immunology, Feb. 2015, vol. 6, Article 39, pp. 1-14.

Yeung et al., "Engineering Human IgG1 Affinity to Human Neonatal Fc Receptor: Impact of Affinity Improvement on Pharmacokinetics in Primates", The Journal of Immunology, 2009, vol. 182 pp. 7663-7671.

Zalevsky et al., "Enhanced Antibody Half-Life Improves In Vivo Activity", Nat Biotechnol. Feb. 2010, vol. 28, No. 2, pp. 157-159.

Hinton, P.R., et al., "Engineered Human IgG Antibodies with Longer Serum Half-lives in Primates," The Journal of Biological Chemistry, Feb. 20, 2004, vol. 279, No. 8, pp. 6213-6216.

\* cited by examiner

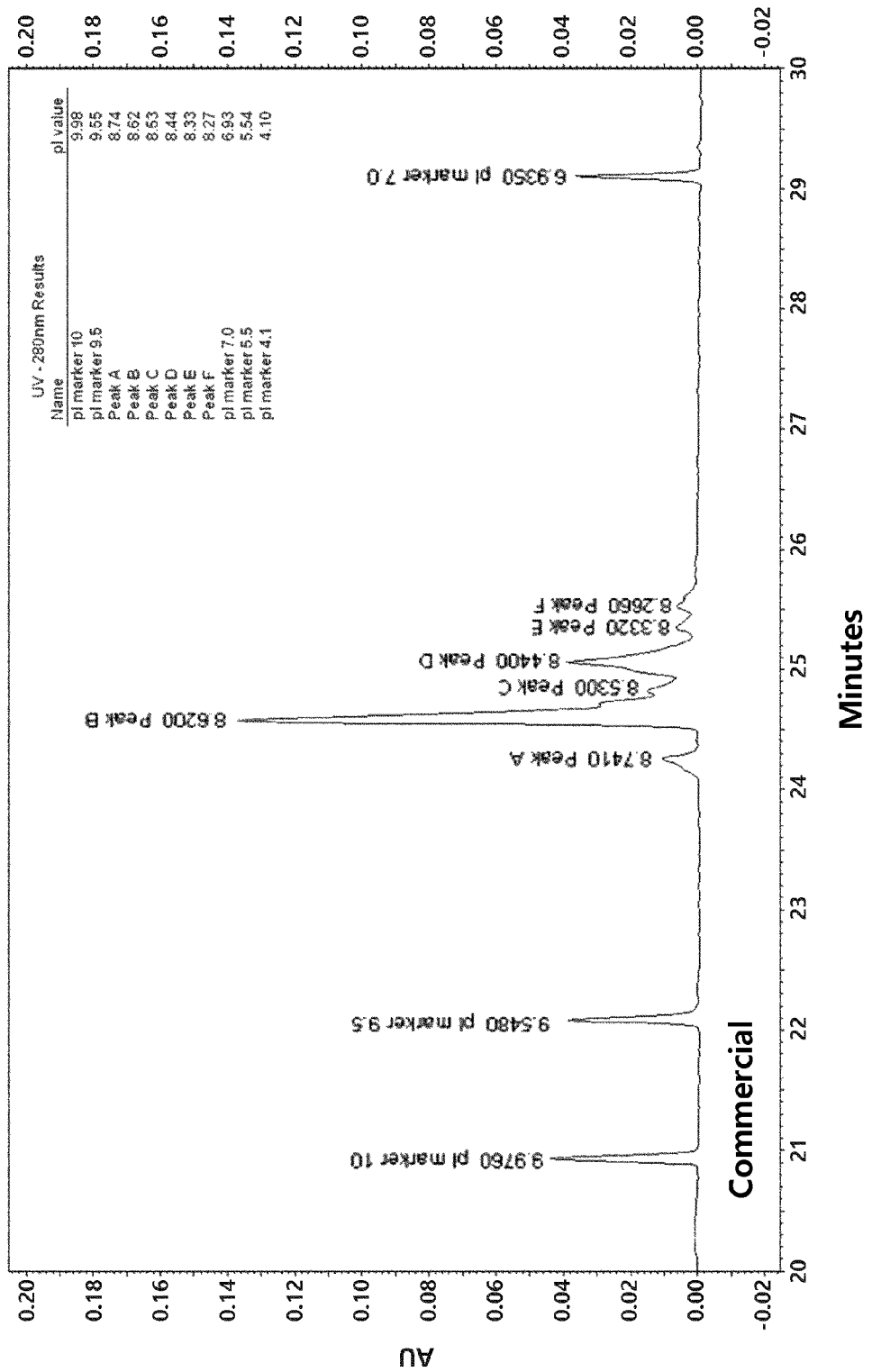
FIG. 8a1

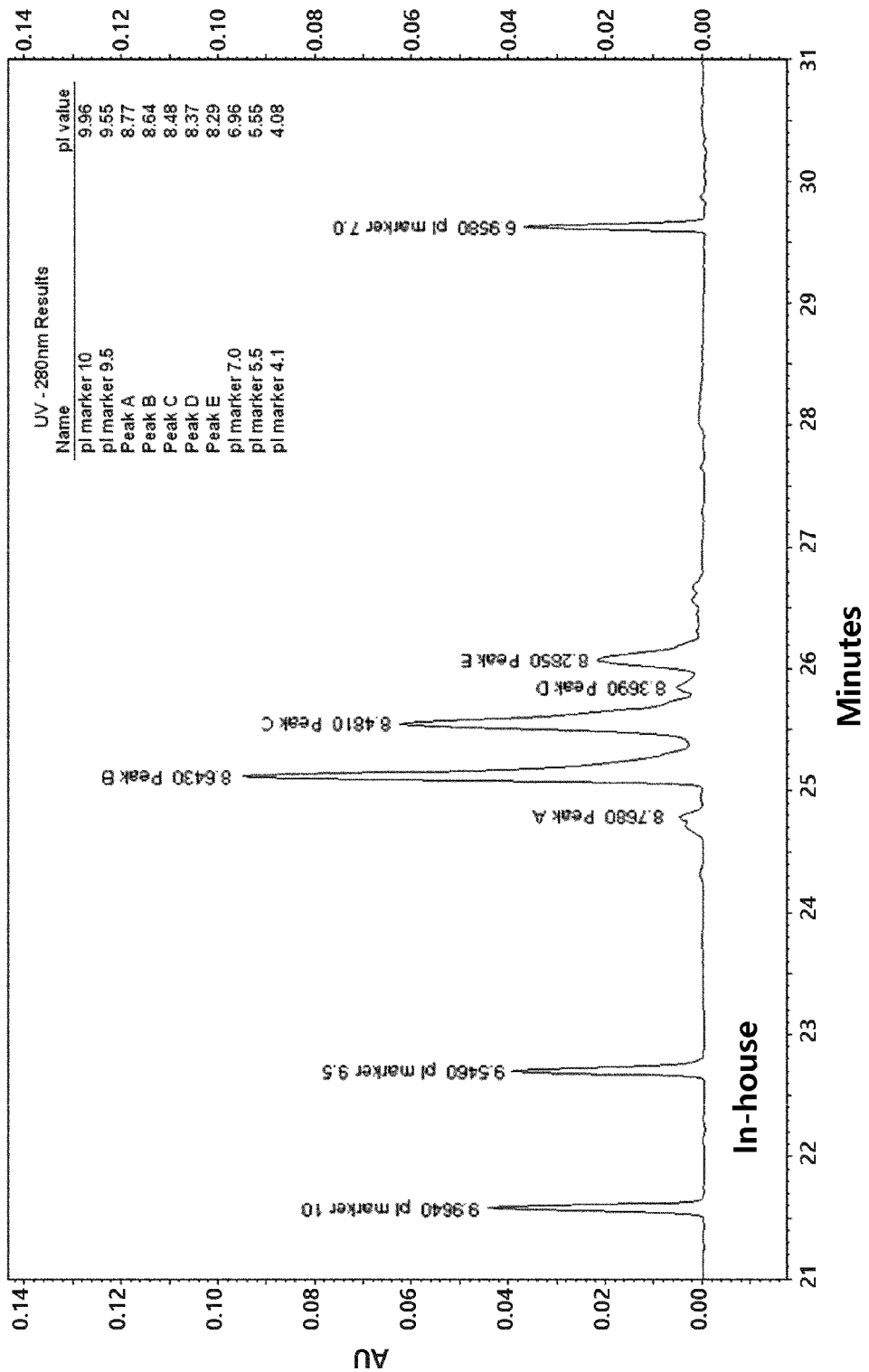
FIG. 8a2

FIG. 10c

|    | Fc variants | Concentration    |
|----|-------------|------------------|
| 1  | EFC 82      | 10mg (3.5mg/ml)  |
| 2  | EFC 29      | 15mg (3.5mg/ml)  |
| 3  | EFC 41      | 12.8mg (3.2mg/ml)|
| 4  | PFC 29      | 15.3mg (5.3mg/ml)|
| 5  | PFC 41      | 12.6mg (3.6mg/ml)|
| 6  | PFC 3       | 15mg (4.7mg/ml)  |
| 7  | EPC 88      | 11mg (3mg/ml)    |
| 8  | YTE         | 13.5mg (5mg/ml)  |
| 9  | M428L       | 14.5mg (5mg/ml)  |
| 10 | LS          | 12.5mg (5mg/ml)  |

FIG. 13a

| Name | $K_D$(nM) |
|---|---|
| Trastuzumab (*commercial*) | 15.03 |
| Trastuzumab (*in-house*) | 16.91 |
| YTE | 5.73 |
| M428L | 9.13 |
| LS | 4.10 |
| PFc3 | 5.60 |
| PFc29 | 6.82 |
| PFc41 | 5.94 |
| PFc41-2 | 10.5 |
| PFc41-3 | 11.1 |
| EFc29 | 7.70 |
| EFc41 | 6.20 |
| EFc82 | 6.68 |
| EFc88 | 6.99 |

ANTIBODY FC VARIANTS FOR INCREASED BLOOD HALF-LIFE

CROSS-REFERENCE TO RELATED APPLICATIONS

This application is a § 371 national stage entry of International Application No. PCT/KR2018/004104, filed on Apr. 6, 2018, which claims priority to Korean Patent Application No. 10-2017-0045142, filed Apr. 7, 2017, and Korean Patent Application No. 10-2017-0047821, filed Apr. 13, 2017, and Korean Patent Application No. 10-2017-0047822, filed Apr. 13, 2017, the entire contents of which are incorporated herein by reference.

TECHNICAL FIELD

The present invention relates to novel antibody Fc variants with increased blood half-life and methods for producing the antibody Fc variants.

SEQUENCE LISTING

The instant application contains a Sequence Listing which has been submitted electronically in ASCII format and is hereby incorporated by reference in its entirety. Said ASCII copy, created on Apr. 3, 2020, is named G1035-15301_SecondRevisedSequenceList.txt and is 24,273 bytes in size.

BACKGROUND ART

With recent advances in biotechnology such as genetic recombination and cell culture, a great deal of research has been conducted on the structure and function of proteins throughout the world. Biotechnology promotes a better understanding of vital phenomena and plays a decisive role in elucidating the mechanism of pathogenesis of various diseases to pave the way for effective diagnosis and treatment of diseases, greatly contributing to an improvement in the quality of life. Particularly, since hybridoma technology for monoclonal antibody production by fusing B cells with myeloma cells was developed in 1975 (Kohler and Milstein, Nature, 256:495-497, 1975), extensive research and development has been conducted on immunotherapy using therapeutic antibodies in clinical applications, including cancer, autoimmune disease, inflammation, cardiovascular disease, and infection.

Therapeutic antibodies have much higher specificity for targets, are less biotoxic, and cause fewer side effects than existing small-molecule drugs. Another advantage of therapeutic antibodies is their long blood half-life (about 3 weeks). Due to these advantages, therapeutic antibodies are considered the most effective approaches for cancer treatment. Indeed, large pharmaceutical companies and research institutes have concentrated their R&D capabilities on therapeutic antibodies that specifically bind to and effectively remove cancer cells, including carcinogenic factors. Roche, Amgen, Johnson & Johnson, Abbott, and BMS are major pharmaceutical companies that are currently developing therapeutic antibody drugs. Particularly, Roche, who developed three innovative therapeutic antibodies, i.e. Herceptin, Avastin, and Rituxan, for applications in anticancer therapy, reached approximately 19.5 billion US dollars in sales for the therapeutic antibodies in 2012 to gain huge profits in the global market and is currently leading the global market for antibody drugs. Johnson & Johnson, who developed Remicade, is rapidly growing in the global market for antibodies due to the increased sales volume of Remicade. Other pharmaceutical companies such as Abbott and BMS are known to possess many therapeutic antibodies in the final stage of development. As a consequence, biomedicines, including therapeutic antibodies that are specific for target diseases and cause few side effects, are rapidly replacing small-molecule medicines that have led the global pharmaceutical market.

The Fc region of an antibody recruits immune leukocytes or serum complement molecules, which in turn triggers the clearance of defective cells such as tumor cells or infected cells. The Fc interface between Cγ2 and Cγ3 domains mediates interactions with the neonatal Fc receptor (FcRn) and its binding recycles endocytosed antibody from the endosome back to the bloodstream (Raghavan et al., 1996, Annu Rev Cell Dev Biol 12: 181-220; Ghetie et al., 2000, Annu Rev Immunol 18: 739-766). This process, coupled with preclusion of kidney filtration due to the large size of the full-length IgG antibody molecule, results in favorable antibody serum half-life in the range of 1-3 weeks. Further, binding of Fc to FcRn plays a key role in antibody transport. Accordingly, the Fc region is crucial for the prolonged serum persistence of circulating antibodies through an intracellular trafficking and recycle mechanism.

The administration of an antibody or an Fc-fusion protein as a therapeutic agent requires a predetermined frequency of injection taking into consideration the half-life of the therapeutic agent. A longer in vivo half-life allows for less frequent injection or lower dosing. Thus, in many clinical studies that are currently underway, many efforts have concentrated on the development of next-generation anticancer therapeutic antibodies and anticancer therapeutic proteins by the introduction of mutations into the Fc domain to increase the half-life of antibodies or the introduction of variants into the Fc domain to achieve a maximal ADCC effect (*Modified from Cancer Immunol Res.* 2015/Thomson Reuters).

However, despite the research groups' efforts aimed at developing some proteins and antibodies with increased binding affinity for FcRn and extended in vivo half-life by introducing some mutations into the Fc domain, a significant increase in in vivo half-life is not yet achieved. Under these circumstances, there is an urgent need to develop optimally mutated antibodies.

The description of the Background Art is merely provided for better understanding the background of the invention and should not be taken as corresponding to the prior art already known to those skilled in the art.

DETAILED DESCRIPTION OF THE INVENTION

Problems to be Solved by the Invention

The present inventors have earnestly conducted research to efficiently increase the in vivo half-life of existing therapeutic proteins or antibodies, and as a result, found that a therapeutic protein or antibody is optimized by substituting a portion of the amino acid sequence of the wild-type Fc domain with a different amino acid sequence so that its blood half-life can be maximized while maintaining its superior activity.

One object of the present invention is to provide a polypeptide including an Fc variant produced by substituting a portion of the amino acid sequence of the Fc domain of a human antibody with a different amino acid sequence.

A further object of the present invention is to provide an antibody including the polypeptide.

Another object of the present invention is to provide a nucleic acid molecule encoding the polypeptide.

Another object of the present invention is to provide a vector including the nucleic acid molecule.

Another object of the present invention is to provide a host cell including the vector.

Another object of the present invention is to provide a composition including the polypeptide, the antibody, the nucleic acid molecule or the vector.

Another object of the present invention is to provide a method for producing the polypeptide or the antibody.

Still another object of the present invention is to provide a method for screening the polypeptide.

Other objects and advantages of the invention become more apparent from the following detailed description, claims, and drawings.

Means for Solving the Problems

One aspect of the present invention provides a polypeptide including an Fc variant produced by substituting a portion of the amino acid sequence of the Fc domain of a human antibody with a different amino acid sequence.

A further aspect of the present invention provides a composition for increasing the blood half-life of a therapeutic antibody or protein, including an Fc variant produced by substituting a portion of the amino acid sequence of the Fc domain of a human antibody with a different amino acid sequence.

The present inventors tried to find an approach for efficiently increasing the in vivo half-life of an existing therapeutic protein or antibody, and as a result, found that a therapeutic protein or antibody including an FC variant produced by substituting and optimizing a portion of the amino acid sequence of the wild-type Fc domain with a different amino acid sequence can achieve a maximum in vivo half-life.

An antibody is a protein that specifically binds to a specific antigen. A natural antibody is a heterodimeric glycoprotein with a molecular weight of about 150,000 daltons that usually consists of two identical light chains (L) and two identical heavy chains (H).

The human antibody used in the present invention belongs to one of the five major classes: IgA, IgD, IgE, IgG, and IgM. The human antibody is preferably an IgG antibody. Papain digestion of antibodies procures two Fab fragments and one Fc fragment, and the Fc region of a human IgG molecule is generated by papain digestion of the N-terminus of Cys 226 (Deisenhofer, *Biochemistry* 20: 2361-2370, 1981).

The antibody Fc domain may be the Fc domain of an IgA, IgM, IgE, IgD or IgG antibody or its modifications. In one embodiment, the domain is the Fc domain of an IgG antibody, for example, an IgG1, IgG2a, IgG2b, IgG3 or IgG4 antibody. In one embodiment, the Fc domain may be an IgG1 Fc domain, for example, the Fc domain of an anti-HER2 antibody, preferably the Fc domain of trastuzumab, more preferably the Fc domain having the sequence set forth in SEQ ID NO: 28. The polypeptide of the present invention may be optionally partially or fully glycosylated. The polypeptide of the present invention may further include one or more regions derived from the antibody in addition to the Fc domain. In addition, the polypeptide of the present invention may include an antigen binding domain derived from the antibody and may form an antibody or antibody-like protein with another polypeptide.

Herein, the amino acid residues of the antibody Fc domain are designated according to the Kabat EU numbering system usually used in the art, as described in Kabat et al., "Sequences of Proteins of Immunological Interest" 5th Ed., U.S. Department of Health and Human Services, NIH Publication No. 91-3242, 1991).

According to a preferred embodiment of the present invention, the substituted Fc variant includes, as an amino acid substitution, M428L according to the Kabat EU numbering system.

According to a preferred embodiment of the present invention, the substituted Fc variant includes, as amino acid substitutions, a) M428L and b) Q311R or L309G according to the Kabat EU numbering system.

According to a preferred embodiment of the present invention, the substituted Fc variant includes, as amino acid substitutions, P228L and M428L according to the Kabat EU numbering system.

According to a preferred embodiment of the present invention, the Fc variant including the amino acid substitutions P228L and M428L includes additional amino acid substitutions at one or more positions selected from the group consisting of positions 234, 264, 269, 292, 309, 342, 359, 364, 368, 388, 394, 422, 434, and 445 according to the Kabat EU numbering system.

The additional amino acid substitutions may be L309R and N434S.

The additional amino acid substitutions may be V264M, L368Q, E388D, V422D, and P445S.

The additional amino acid substitutions may be R292L, T359A, and S364G.

The additional amino acid substitutions may be L234F, E269D, Q342L, E388D, and T394A.

According to a preferred embodiment of the present invention, the substituted Fc variant includes, as amino acid substitutions, a) M428L and b) P230Q or P230S according to the Kabat EU numbering system.

According to a preferred embodiment of the present invention, the substituted Fc variant including the amino acid substitutions a) M428L and b) P230Q or P230S includes additional amino acid substitutions at one or more positions selected from the group consisting of positions 243, 246, 295, 320, 356, 361, 384, and 405 according to Kabat EU numbering system.

The additional amino acid substitutions may be F243Y, K246E, N361S, and N384I.

The additional amino acid substitutions may be Q295L, K320M, D356E, and F405I.

The present invention is directed to an Fc variant including one or more amino acid substitutions that regulate its binding to and dissociation from the neonatal Fc receptor (FcRn). Particularly, the Fc variant of the present invention or its functional variant exhibits increased binding affinity for FcRn under acidic conditions (at a pH lower than 7) and very low binding force to FcRn under neutral pH conditions.

The therapeutic antibody whose half-life is to be increased is not particularly limited and examples thereof include polyclonal antibodies, monoclonal antibodies, minibodies, domain antibodies, bispecific antibodies, antibody mimetics, chimeric antibodies, antibody conjugates, human antibodies, humanized antibodies, and their fragments.

As the monoclonal antibodies, there may be mentioned, for example: human antibodies, such as panitumumab (Vectibix), ofatumumab (Arzerra), golimumab (Simponi), and ipilimumab (Yervoy); humanized antibodies, such as tocilizumab (Actemra), trastuzumab (Herceptin), bevacizumab (Avastin), omalizumab (Xolair), mepolizumab (Bosatria), gemtuzumab ozogamicin (Mylotarg), palivizumab (Synagis), ranibizumab (Lucentis), certolizumab (Cimzia), ocrelizumab, mogamulizumab (Poteligeo), and eculizumab (Soliris); and chimeric antibodies, such as rituximab (Rituxan), cetuximab (Erbitux), infliximab (Remicade), and basiliximab (Simulect).

The therapeutic protein whose half-life is to be increased is not particularly limited and examples thereof include: hormones, such as insulin; cytokines, such as growth factors, interferons, interleukins, erythropoietin, neutrophil growth factors, and transforming growth factors; Fc fusion proteins, such as etanercept (Enbrel), aflibercept (Eylea, Zaltrap), abatacept (Orencia), alefacept (Amevive), belatacept (Nulojix), and rilonacept (Arcalyst); therapeutic peptides, such as teriparatide (Forteo), exenatide (Byetta), liraglutide (Victoza), lanreotide (Somatuline), pramlintide (Symlin), and enfuvirtide (Fuzeon); and polypeptides including, in part or in whole, VEGF receptors, Her2 receptors, G-protein-coupled receptors, and cell surface receptors of ion channels.

The half-life of the therapeutic antibody or protein can be extended by binding to the polypeptide of the present invention or a nucleic acid encoding the polypeptide or introducing into a vector expressing the nucleic acid.

According to a preferred embodiment of the present invention, the binding affinity of the Fc variant for FcRn at a pH of 5.6 to 6.4 (preferably 5.8 to 6.2) is higher by at least 10%, at least 20%, at least 30%, at least 40%, at least 50%, at least 60%, at least 70%, at least 80%, at least 90% or at least 100% than that of the wild-type Fc domain or by at least 2 times, at least 3 times, at least 4 times, at least 5 times, at least 6 times, at least 7 times, at least 8 times, at least 9 times, at least 10 times, at least 20 times, at least 30 times, at least 40 times, at least 50 times, at least 60 times, at least 70 times, at least 80 times, at least 90 times or at least 100 times than that of the wild-type Fc domain.

According to a preferred embodiment of the present invention, the degree of dissociation of the Fc variant from the neonatal Fc receptor (FcRn) at a pH of 7.0 to 7.8 (preferably 7.2 to 7.6) may be the same as or not substantially different from that of the wild-type Fc domain.

According to one embodiment of the present invention, the substituted Fc variant exhibits much higher binding affinity under weakly acidic conditions (for example, at a pH of 5.8 to 6.2) than the wild-type Fc or other developed Fc variants and its degree of dissociation under neutral conditions (for example, at a pH of 7.4) is the same as or substantially equivalent to or higher than that of the wild-type Fc or other developed Fc variants (see Examples 4 and 8).

According to a preferred embodiment of the present invention, the substituted Fc variant has a long half-life compared to the wild type.

The half-life of the substituted Fc variant according to the present invention may be longer by at least 10%, at least 20%, at least 30%, at least 40%, at least 50%, at least 60%, at least 70%, at least 80%, at least 90% or at least 100% than that of the wild-type Fc domain or at least two times, at least 3 times, at least 4 times, at least 5 times, at least 6 times, at least 7 times, at least 8 times, at least 9 times or at least 10 times that of the wild-type Fc domain.

According to one embodiment of the present invention, the substituted Fc variant has a significantly improved in vivo half-life compared to the wild type (see Example 11 and Table 3).

By "Fc gamma receptor" or "FcγR" as used herein is meant any member of a family of proteins that bind to the Fc region of an IgG antibody and are encoded by the FcγR gene. Examples of such Fc gamma receptors or FcγRs include, but are not limited to: FcγRI(CD64), including FcγRIa, FcγRIb, and FcγRIc; FcγRII(CD32), including FcγRIIa, FcγRIIb, and FcγRIIc; FcγRIII(CD16), including FcγRIIIa and FcγRIIIb; and undiscovered FcγRs. The FcγR may be derived from mammalian organisms, including humans, mice, rats, rabbits, and monkeys, and other organisms.

By "FcRn" or "neonatal Fc Receptor" as used herein is meant a protein that binds to the Fc region of an IgG antibody and is encoded at least partially by the FcRn gene. The FcRn may be derived from mammalian organisms, including humans, mice, rats, rabbits, and monkeys, and other organisms. The functional FcRn protein includes two polypeptides, which are referred to as heavy and light chains. The light chain is beta-2-microglobulin and the heavy chain is encoded by the FcRn gene.

Another aspect of the present invention provides an antibody including the polypeptide.

As used herein, the term "antibody" refers to a polyclonal antibody, a monoclonal antibody, a minibody, a domain antibody, a bispecific antibody, an antibody mimetic, a chimeric antibody, an antibody conjugate, a human antibody, a humanized antibody or its fragment (for example, an antigen binding antibody fragment).

According to a preferred embodiment of the present invention, the half-life of the Fc domain or the polypeptide including the Fc domain can be maximized by optimization of the corresponding antibody Fc regions (for example, M428L and Q311R; or M428L and L309G).

Another aspect of the present invention provides a nucleic acid molecule encoding the polypeptide, a vector including the nucleic acid molecule or a host cell including the vector.

The nucleic acid molecule of the present invention may be an isolated or recombinant nucleic acid molecule. Examples of such nucleic acids include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be understood as a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancer need is not necessarily contiguous. The linkage is performed by ligation at a convenient restriction enzyme site. In the case where this site does not exist, a synthetic oligonucleotide adaptor or a linker is used according to a suitable method known in the art.

As used herein, the term "vector" is used to refer to a carrier into which a nucleic acid sequence can be inserted for introduction into a cell where it can be replicated. A nucleic acid sequence can be "exogenous," or "heterologous". Vectors include plasmids, cosmids and viruses (e.g., bacteriophage). One of skill in the art may construct a vector through standard recombinant techniques, which are described in Maniatis et al., Molecular Cloning, A Laboratory Manual, Cold Spring Harbor Press, Cold Spring Harbor, N.Y., 1988; and Ausubel et al., In: *Current Protocols in Molecular Biology*, John, Wiley & Sons, Inc, N Y, 1994).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences". In addition to control sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

The host cell of the present invention is preferably a bacterial cell, CHO cell, HeLa cell, HEK293 cell, BHK-21 cell, COS7 cell, COP5 cell, A549 cell or NIH3T3 cell, but is not limited thereto.

Another aspect of the present invention provides a method for producing a polypeptide including a human antibody Fc variant, including: a) culturing a host cell including a vector including a nucleic acid molecule encoding the polypeptide; and b) collecting the polypeptide expressed by the host cell.

Another aspect of the present invention provides a method for producing an antibody, including: a) culturing a host cell expressing an antibody including the polypeptide; and b) purifying the antibody expressed by the host cell.

In the method of the present invention, the antibody may be purified by filtration, HPLC, anion exchange or cation exchange, high-performance liquid chromatography (HPLC), affinity chromatography or a combination thereof, preferably affinity chromatography using Protein A.

Another aspect of the present invention provides a method for screening a polypeptide including an Fc variant, including: constructing a library of Fc variants including, as a mutation, M428L according to the Kabat EU numbering system; and b) sorting an Fc variant having a higher affinity for FcRn at a pH of 5.6 to 6.4 than the wild type from the Fc variants including the M428L mutation.

The Fc variants including the M428L mutation may include at least one additional amino acid substitution.

According to a preferred embodiment of the present invention, the additional amino acid substitution includes Q311R or L309G as a mutation.

According to a preferred embodiment of the present invention, the additional amino acid substitution includes P228L as a mutation.

The Fc variants including the P228L mutation may include at least one additional amino acid substitution.

The additional amino acid substitution is not particularly limited but is preferably an amino acid mutation at at least one position selected from the group consisting of positions 234, 264, 269, 292, 309, 342, 359, 364, 368, 388, 394, 422, 434, and 445 according to the Kabat EU numbering system.

According to a preferred embodiment of the present invention, the additional amino acid substitution includes P230Q or P230S as a mutation.

The Fc variants including the P230 mutation may include at least one additional amino acid substitution.

The additional amino acid substitution is not particularly limited but is preferably an amino acid mutation at at least one position selected from the group consisting of positions 243, 246, 295, 320, 356, 361, 384, and 405 according to the Kabat EU numbering system.

The screening method of the present invention can use fluorescence-activated cell sorting (FACS) or automated flow cytometry. Instruments for flow cytometry are well known to those skilled in the art. Examples of such instruments include FACSAria, FACS Star Plus, FACScan, and FACSort (Becton Dickinson, Foster City, Calif.), Epics C (Coulter Epics Division, Hialeah, Fla.), MOFLO (Cytomation, Colorado Springs, Colo), and MOFLO-XDP (Beckman Coulter, Indianapolis, Ind.). Flow cytometry generally involves the separation of cells or other particles in a liquid sample. Typically, the purpose of flow cytometry is to analyze the separated particles for one or more characteristics thereof, for example, presence of a labeled ligand or other molecule. The particles are passed one by one by the sensor and are sorted based on size, refraction, light scattering, opacity, roughness, shape, fluorescence, etc.

Another aspect of the present invention provides a composition including the polypeptide including the Fc variant including one or more amino acid substitutions, the antibody, the nucleic acid molecule or the vector.

According to a preferred embodiment of the present invention, the composition is a pharmaceutical composition for preventing or treating cancer.

According to a preferred embodiment of the present invention, the pharmaceutical composition (or the polypeptide, the antibody, the nucleic acid molecule or the vector) recognizes a cancer antigen.

According to one embodiment of the present invention, the Fc variant has antibody dependent cellular cytotoxicity (ADCC) activity comparable or superior to that of a control group (for example, trastuzumab), achieving significantly increased half-life and high anticancer activity (see Example 13 and FIG. 18).

The pharmaceutical composition of the present invention may include (a) the polypeptide, the antibody, the nucleic acid molecule encoding the polypeptide or the vector including the nucleic acid molecule and (b) a pharmaceutically acceptable carrier.

Yet another aspect of the present invention provides a method for preventing or treating cancer, including administering the pharmaceutical composition to a subject.

The type of the cancer to be prevented or treated by the method of the present invention is not limited. The pharmaceutical composition of the present invention can be administered to treat a number of cancers, including leukemias and lymphomas such as acute lymphocytic leukemia, acute nonlymphocytic leukemias, chronic lymphocytic leukemia, chronic myelogenous leukemia, Hodgkin's Disease, non-Hodgkin's lymphomas, multiple myeloma, childhood solid tumors such as brain tumors, neuroblastoma, retinoblastoma, Wilms Tumor, bone tumors, and soft-tissue sarcomas, common solid tumors of adults such as lung cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The pharmaceutically acceptable carrier of the pharmaceutical composition according to the present invention may be any of those known in the art. Examples of carriers suitable for use in the pharmaceutical composition of the present invention include, but are not limited to, lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil. The pharmaceutical composition of the present invention may further include at least one additive selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences (19th ed., 1995).

The pharmaceutical composition of the present invention can be administered orally or parenterally, preferably parenterally. For example, the pharmaceutical composition of the present invention may be administered by intravenous, local or intraperitoneal injection.

The subject is not particularly limited but is preferably construed to include vertebrates, more preferably primates, including humans and chimpanzees, household pets, including dogs and cats, livestock, including cattle, horses, sheep, and goats, and rodents, including mice and rats.

A suitable dose of the pharmaceutical composition according to the present invention depends on a variety of factors such as formulation, mode of administration, age, body weight, sex, and pathological condition of the patient, diet, time and route of administration, rate of excretion, and responsiveness. A physician having ordinary skill in the art can readily determine and prescribe an effective dose of the pharmaceutical composition according to the present invention for the desired treatment or prevention. According to a preferred embodiment of the present invention, the daily dose of the pharmaceutical composition according to the present invention is from 0.0001 to 100 mg/kg.

The pharmaceutical composition of the present invention can be prepared in unit dosage forms or dispensed in multi-dose containers with a pharmaceutically acceptable carrier and/or excipient by a suitable method which can be easily carried out by one having ordinary skill in the art. The pharmaceutical composition of the present invention may be in the form of a solution, suspension or emulsion in an oil or aqueous medium. The pharmaceutical composition of the present invention may be in the form of an extract, powder, granule, tablet or capsule. The pharmaceutical composition of the present invention may further include a dispersant or a stabilizer.

The pharmaceutical composition of the present invention can be used for a single therapy. Alternatively, the pharmaceutical composition of the present invention may be used in combination with general chemotherapy or radiotherapy. This combined therapy is more effective for cancer treatment. Chemotherapeutic agents that can be used with the composition of the present invention include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastine, and methotrexate, and the like. Radiation therapies that can be used with the composition of the present invention include X-ray irradiation and γ-ray irradiation.

Effects of the Invention

The features and advantages of the present invention are summarized as follows.

(i) The present invention provides a polypeptide including an Fc variant produced by substituting a portion of the amino acid sequence of the Fc domain of a human antibody with a different amino acid sequence.

(ii) The present invention also provides a method for producing the polypeptide or an antibody including the polypeptide.

(iii) The Fc variant of the present invention is suitable for use in the treatment of cancer because its in vivo half-life can be maximized by optimization of the portion of the amino acid sequence.

BEST MODE FOR CARRYING OUT THE INVENTION

The present invention will be explained in more detail with reference to the following examples. It will be evident to those skilled in the art that the scope of the present invention is not limited by these examples according to the gist of the present invention.

EXAMPLES

Figure 1:
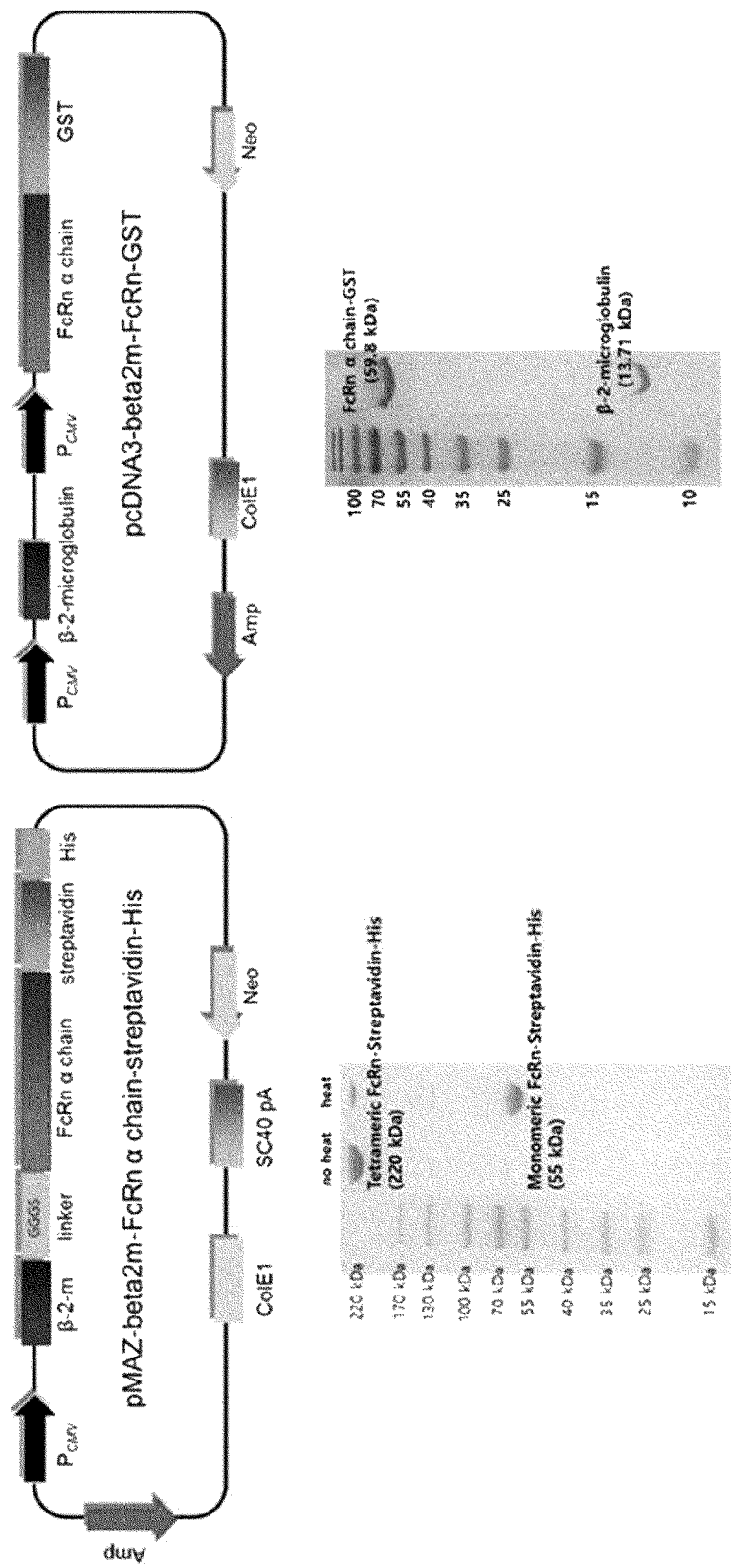
FIG. 1 shows expression vectors for expression and purification of tetrameric FcRn and dimeric FcRn and SDS-PAGE gels after purification.

Example 1: Expression and Purification of Neonatal Fc Receptor (FcRn) for Searching Library of Fc Variants Tetrameric FcRn and dimeric FcRn for searching Fc variants with improved pH-dependent binding force to FcRn were expressed and purified. To this end, expression vectors were prepared (FIG. 1). pMAZ-β2microglobulin-GSlinker-FcRnα-chain-streptavidin-His was constructed as a DNA plasmid to obtain tetrameric FcRn. The DNA was co-transfected into HEK 293F cells and temporarily expressed at a level of 300 ml. The resulting culture medium was centrifuged at 7000 rpm for 10 min. The collected supernatant was equilibrated with 25×PBS and filtered with a 0.2 m bottle top filter (Merck Millipore). After equilibration with PBS, FcRn was allowed to bind to Ni-NTA resin (Qiagen) at 4° C. for 16 h. The FcRn-bound resin was loaded onto a column and the column was eluted with 50 ml of wash-1 buffer (PBS), 25 ml of wash-2 buffer (PBS+10 mM imidazole), 25 ml of wash-3 buffer (PBS+20 mM imidazole), and 200 μl of wash-4 buffer (PBS+250 mM imidazole) to remove proteins other than tFcRn. Then, 2.5 ml of elution buffer (PBS+250 mM imidazole) was allowed to flow through the column to obtain tFcRn. The buffer was replaced with a new one using centrifugal filter units (Merck Millipore). Dimeric FcRn was obtained from pcDNA-FcRnα-chain-GST-β2 microglobulin plasmid, which was received from the University of Oslo. The DNA was co-transfected into HEK 293F cells and temporarily expressed at a level of 300 ml. The resulting culture medium was centrifuged at 7000 rpm for 10 min. The collected supernatant was equilibrated with 25×PBS and filtered with a 0.2 m bottle top filter (Merck Millipore). After equilibration with PBS, FcRn was allowed to bind to Glutathione Agarose 4B (incospharm) at 4° C. for 16 h. The FcRn-bound resin was loaded onto a column and the column was eluted with 10 ml of wash buffer (PBS) to remove proteins other than dFcRn. Then, 2.5 ml of elution buffer (50 mM Tris-HCl+10 mM GSH pH 8.0) was allowed to flow through the column. The buffer was replaced with a new one using centrifugal filter units 3K (Merck Millipore). The sizes of the tetrameric FcRn and dimeric FcRn after purification were determined using SDS-PAGE gels (FIG. 1). The purified tetrameric FcRn and dimeric FcRn were fluorescently labeled with Alexa 488 for fluorescence detection.

Figure 2:
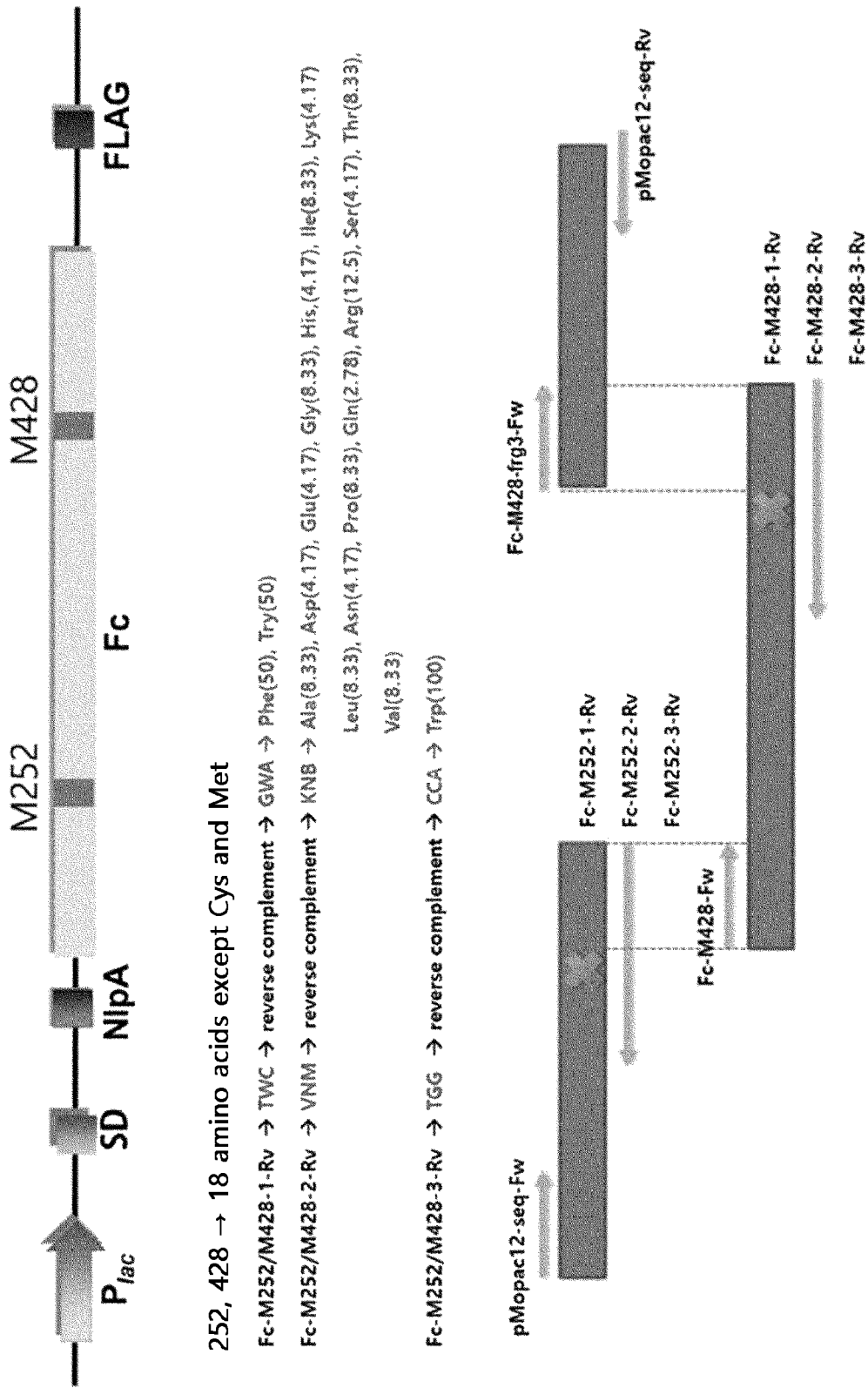
FIG. 2 is a schematic diagram of a library constructed such that 18 amino acids are contained at positions M252 and M428.

Example 2: Construction of 2M Library of Fc Variants pMopac12-NlpA-Fc-FLAG was constructed from the gene (SEQ ID NO: 29) of the Fc domain of trastuzumab using SfiI restriction enzyme. Based on the vector, library inserts were constructed using pMopac12-seq-Fw, Fc-M252-1-Rv, Fc-M252-2-Rv, Fc-M252-3-Rv, Fc-M428-Fw, Fc-M428-1-Rv, Fc-M428-2-Rv, Fc-M428-3-Rv, Fc-M428-frg3-Fw, and pMopac12-seq-Rv primers such that two Met residues in the Fc were substituted with 18 different amino acids except Cys and Met (Table 1 and FIG. 2). The inserts were treated with SfiI restriction enzyme and ligated with the vector treated with the same SfiI. Thereafter, the ligated inserts were transformed into *E. coli* Judel ((F'[Tn10 (Tet$^r$)proAB$^+$lacI$^q$Δ(lacZ)M15] mcrAΔ(mrr-hsdRMS-mcrBC)Φ80dlacZΔM15 ΔlacX74 deoR recA1 araD139Δ (ara leu)7697 galU galKrpsLendA1nupG) to establish a large 2M library of Fc variants (library size: 1×10$^9$).

TABLE 1

| | |
|---|---|
| pMopac12-seq-Fw | 5'-CCAGGCTTTACACTTTATGC-3' |
| Fc-M252-1-Rv | 5'-CCTCAGGGGTCCGGGAGATGWAGAGGGTGTCCTTGGGTTTTGGG-3' |
| Fc-M252-2-Rv | 5'-CCTCAGGGGTCCGGGAGATKNBGAGGGTGTCCTTGGGTTTTGGG-3' |
| Fc-M252-3-Rv | 5'-CCTCAGGGGTCCGGGAGATCCAGAGGGTGTCCTTGGGTTTTGGG-3' |
| Fc-M428-Fw | 5'-ATCTCCCGGACCCCTGAGG-3' |
| Fc-M428-1-Rv | 5'-GTAGTGGTTGTGCAGAGCCTCATGGWACACGGAGCATGAGAAGACGTTCC-3' |
| Fc-M428-2-Rv | 5'-GTAGTGGTTGTGCAGAGCCTCATGKNBCACGGAGCATGAGAAGACGTTCC-3' |
| Fc-M428-3-Rv | 5'-GTAGTGGTTGTGCAGAGCCTCATGCCACACGGAGCATGAGAAGACGTTCC-3' |
| Fc-M428-frg3-Fw | 5'-CATGAGGCTCTGCACAACCACTAC-3' |
| pMopac12-seq-Rv | 5'-CTGCCCATGTTGACGATTG-3' |
| fC-Sub#0-Rv | 5'-GTCCTTGGGTTTTGGGGGGAAG-3' |
| Fc-Sub#1-1-Fw | 5'-CTTCCCCCCAAAACCCAAGGACNNKCTCATGATCTCCCGGACCCCTGAGGTCACATGCG-3' |
| Fc-Sub#1-2-Fw | 5'-CTTCCCCCCAAAACCCAAGGACACCNNKATGATCTCCCGGACCCCTGAGGTCACATGCG-3' |
| Fc-Sub#1-3-Fw | 5'-CTTCCCCCCAAAACCCAAGGACACCCTCATGNNKTCCCGGACCCCTGAGGTCACATGCG-3' |

TABLE 1-continued

| | |
|---|---|
| Fc-Sub#1-4-Fw | 5'-CTTCCCCCCAAAACCCAAGGACACCCTCATGATCNNKCGGACCCCTGAGGTCACATGCG-3' |
| Fc-Sub#1-5-Fw | 5'-CTTCCCCCCAAAACCCAAGGACACCCTCATGATCTCCNNKACCCCTGAGGTCACATGCG-3' |
| Fc-Sub#1-Rv | 5'-GACGGTGAGGACGCTGACC-3' |
| Fc-Sub#2-1-Fw | 5'-GGTCAGCGTCCTCACCGTCNNKCACCAGGACTGGCTGAATGGCAAGGAGTACAAGTGCAAGG-3' |
| Fc-Sub#2-2-Fw | 5'-GGTCAGCGTCCTCACCGTCCTGCACNNKGACTGGCTGAATGGCAAGGAGTACAAGTGCAAGG-3' |
| Fc-Sub#2-3-Fw | 5'-GGTCAGCGTCCTCACCGTCCTGCACCAGGACTGGNNKAATGGCAAGGAGTACAAGTGCAAGG-3' |
| Fc-Sub#2-Rv | 5'-CACGGAGCATGAGAAGACGTTCC-3' |
| Fc-Sub#3-1-Fw | 5'-GGAACGTCTTCTCATGCTCCGTGCTGCATNNKGCTCTGCACAACCACTACACGCAGAAGAGCCTCTCCCTG-3' |
| Fc-Sub#3-2-Fw | 5'-GGACGTCTTCTCATGCTCCGTGCTGCATGAGGCTNNKCACAACCACTACACGCAGAAGAGCCTCTCCCTG-3' |
| Fc-Sub#3-3-Fw | 5'-GGAACGTCTTCTCATGCTCCGTGCTGCATGAGGCTCTGCACNNKCACTACACGCAGAAGAGCCTCTCCCTG-3' |
| Fc-Sub#3-4-Fw | 5'-GGAACGTCTTCTCATGCTCCGTGCTGCATGAGGCTCTGCACAACCACNNKACGCAGAAGAGCCTCTCCCTG-3' |
| ep-Fc-Fw | 5'-CCAGCCGGCCATGGCG-3' |
| ep-Fc-Rv | 5'-GAATTCGGCCCCCGAGGCCCC-3' |

Primers used for cloning (SEQ ID NOS: 1-27)

Figure 3:
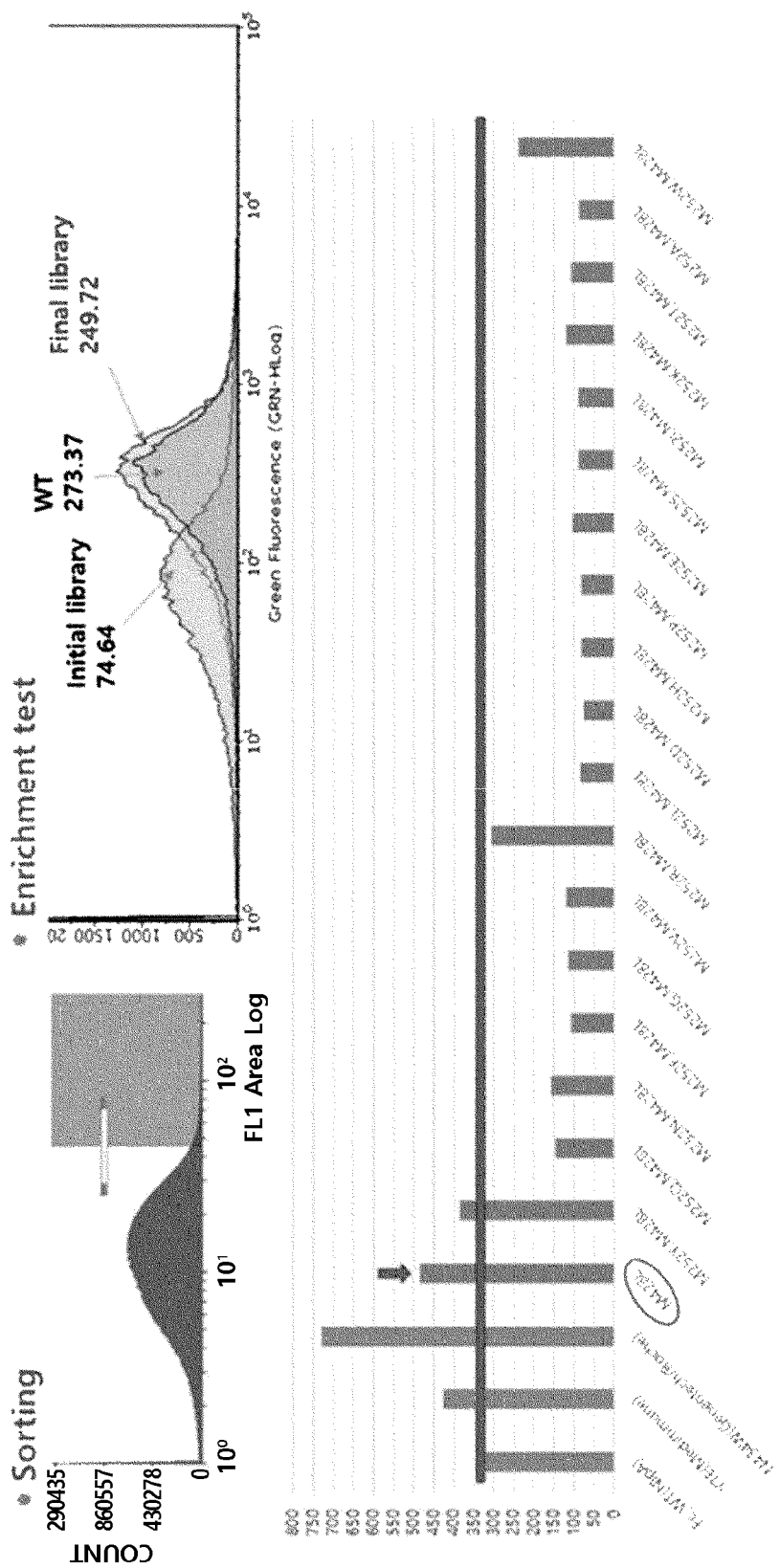
FIG. 3 shows a 2M library search process and a sorted M428L variant.

Example 3: Search Against the 2M Library of Fc Variants Based on Bacterial Culture and Flow Cytometry In this example, a search was conducted against the established 2M library of Fc variants. Specifically, 1 ml of Fc variant library cells transformed into *E. coli* Jude 1 cells were cultured with shaking in Terrific broth (TB) medium supplemented with 2% (w/v) glucose and chloramphenicol (40 μg/mL) as an antibiotic at 37° C. and 250 rpm for 4 h. After shaking culture, the library cells were inoculated into TB medium in a ratio of 1:100 and cultured with shaking at 250 rpm and 37° C. until an OD600 of 0.5 was reached. Thereafter, culture was further performed at 25° C. for 20 min for cooling and 1 mM isopropyl-1-thio-β-D-galactopyranoside (IPTG) was added to induce expression. After completion of the culture, the collected cells were divided into equal amounts based on OD600 normalization, followed by centrifugation at 14000 rpm for 1 min. The harvested cells were resuspended in 1 ml of 10 mM Tris-HCl (pH 8.0) and washed twice by centrifugation for 1 min. Cells were resuspended in 1 ml of STE (0.5 M sucrose, 10 mM Tris-HCl, 10 mM EDTA (pH 8.0)) and centrifuged at 37° C. for 30 min to remove the outer membrane. The supernatant was discarded by centrifugation and 1 ml of Solution A (0.5 M sucrose, 20 mM MgCl$_2$, 10 mM MOPS (pH 6.8)) was added, followed by resuspension and centrifugation. Cells were resuspended in 1 ml of a mixture of 1 ml of Solution A and 20 μl of 50 mg/ml lysozyme solution, followed by centrifugation at 37° C. for 15 min to remove the peptidoglycan layer. The supernatant was removed and cells were resuspended in 1 ml of PBS. 300 μl of the suspension was added with 700 μl of PBS and fluorescently labeled tetrameric FcγRIIIa-Alexa 488 fluor probe and centrifuged at room temperature to label the fluorescent probe with spheroplast. After the labeling, cells were washed once with 1 ml of PBS and sorting was performed by flow cytometry (S3 sortor (Bio-rad)) to collect the top 3% highly fluorescent cells. The sorted cells were resorted for higher purity. For the resorted sample, genes were amplified by PCR using Taq polymerase (Biosesang) with pMopac12-seq-Fw and pMopac12-seq-Rv primers, followed by a series of processes, including treatment with SfiI restriction enzyme, ligation, and transformation, to construct sub-libraries in which the genes of the sorted cells were amplified. A total of 2 rounds of this procedure was performed. Thereafter, the resulting 40 clones were individually analyzed and an M428L variant with higher affinity for FcRn at pH 5.8 than the wild-type Fc was sorted (FIG. 3).

Example 3: Construction of Error Library and Point Library of Fc Variants

Figure 4:
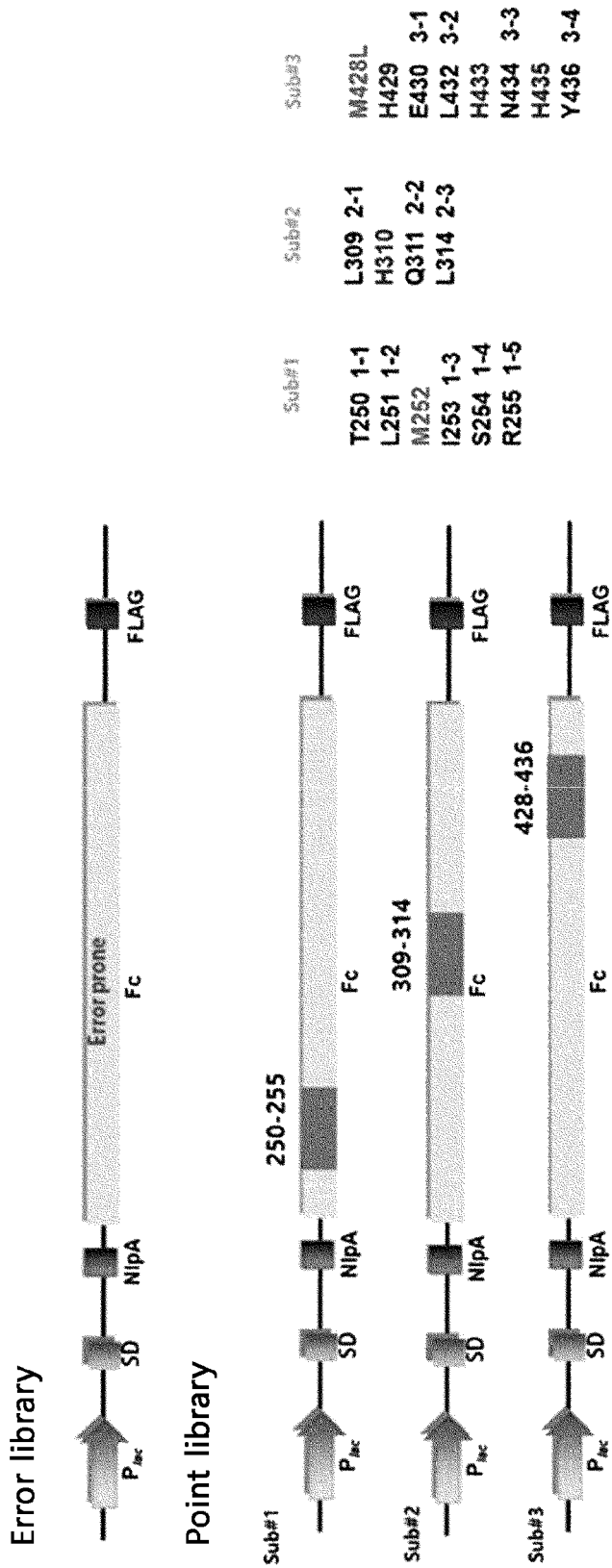
FIG. 4 schematically shows an error library and a point library constructed based on M428L.
Figure 5A:
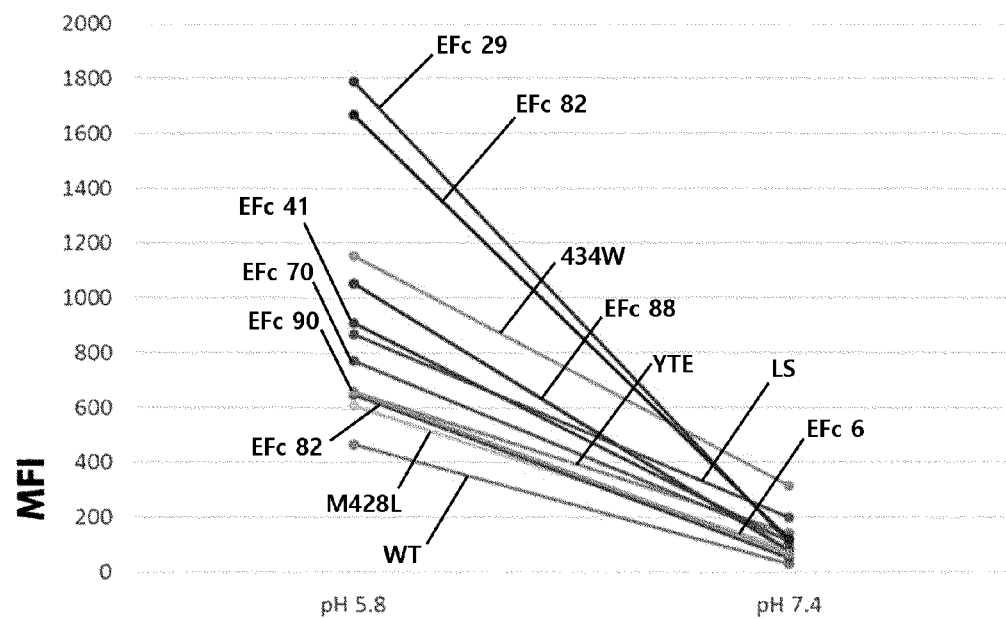
FIG. 5 shows FACS fluorescence intensities of variants sorted from (5a) an error library and (5b) a point library.
Figure 5A:
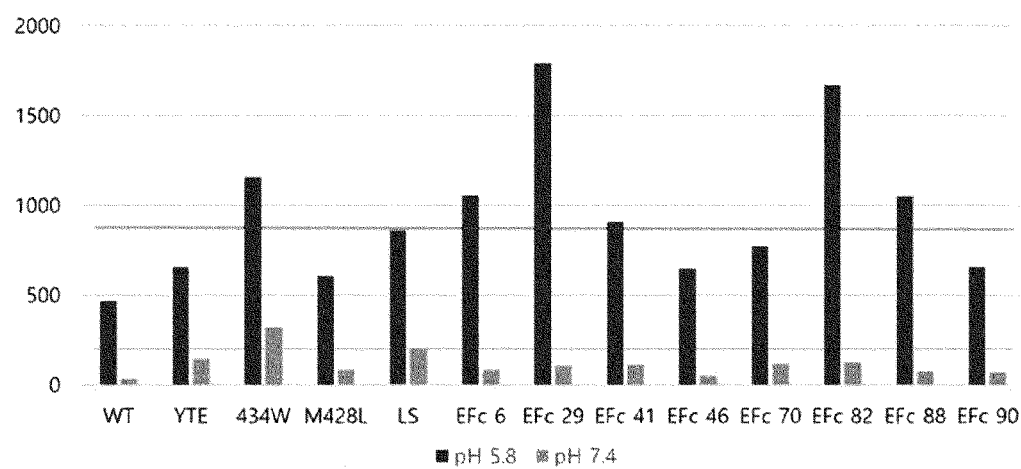
Figure 5B:
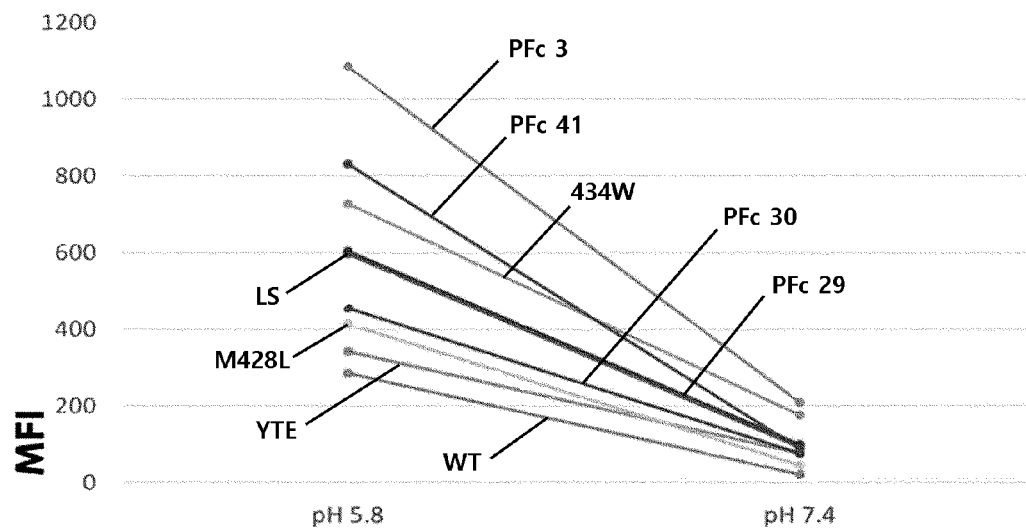
Figure 5B:
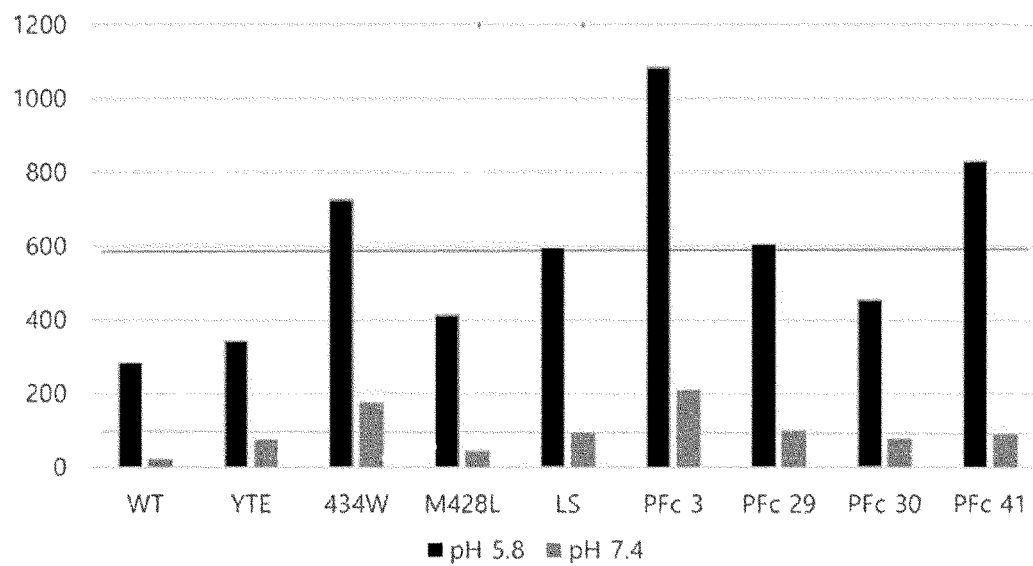

Two additional libraries were constructed using the sorted M428L as a template. First, mutations were introduced into Fc by error prone PCR to construct an error library. The library (size: 2×10$^8$) was constructed using ep-Fc-Fw and ep-Fc-Rv primers at such an error rate that 0.3% error (2.04 bp) was contained in Fc (680 bp). Second, M428L was used as a template to construct a point library. The library was constructed using pMopac12-seq-Fw, pMopac12-seq-Rv, Fc-Sub #0-Rv, Fc-Sub #1-1-Fw, Fc-Sub #1-2-Fw, Fc-Sub #1-3-Fw, Fc-Sub #1-4-Fw, Fc-Sub #1-5-Fw, Fc-Sub #1-Rv, Fc-Sub #2-1-Fw, Fc-Sub #2-2-Fw, Fc-Sub #2-3-Fw, Fc-Sub #2-Rv, Fc-Sub #3-1-Fw, Fc-Sub #3-2-Fw, Fc-Sub #3-3-Fw, and Fc-Sub #3-4-Fw primers such that mutations were randomly introduced into selected regions where Fc were bound to FcRn (FIG. 4). Thereafter, a library of Fc variants was established by transformation into Jude1 in the same manner as described above.

Example 4: Search Against the Error and Point Libraries of Fc Variants Based on Bacterial Culture and Flow Cytometry and Sorting of Variants, Including PFc3, PFc29, PFc41, EFc29, EFc41, EFc82, and EFc88

The above sorting and resorting procedure was performed for the additional error and point libraries constructed based on the sorted M428L. 5 rounds of sorting and resorting were repeated for the error library and only one round of sorting was performed for the point library. A group of about 100 clones from each of the two libraries were individually analyzed and Fc variants having high affinity for FcRn at pH 5.8 and low affinity for FcRn at pH 7.4 were sorted. FACS analysis revealed that EFc6, EFc29, EFc41, EFc46, EFc70, EFc90 EFc82, and EFc88 sorted from the error library showed higher fluorescence intensities at pH 5.8 than the wild-type Fc and conventional variants, including YTE from Medimmune (Gabriel J. Robbie et al., *Antimicrob Agents Chemother.* 2013 December; 57(12): 6147-6153) and LS from Xencor (U.S. Pat. No. 8,324,351). EFc6, EFc29, EFc41, EFc82, and EFc88 were found to show lower fluorescence intensities at pH 7.4 than LS. In addition, PFc3, PFc29, and PFc41 variants sorted from the point library showed higher fluorescence intensities at pH 5.8 than YTE and LS. PFc30 showed a lower fluorescence intensity at pH 5.8 than YTE and LS. PFc29 and PFc41 showed lower fluorescence intensities at pH 7.4 than LS. Finally, EFc6, EFc29, EFc41, EFc82, EFc88, PFc3, PFc29, and PFc41 were selected because they are expected to increase blood half-lives (Table 2 and FIG. 5).

TABLE 2

| Name of Fc variant | Positions of Fc variants and substituted amino acids |
|---|---|
| PFc 3 (SEQ ID NO: 30) | P228L/L309R/M428L/N434S |
| PFc 29 (SEQ ID NO: 31) | Q311R/M428L |
| PFc 41 (SEQ ID NO: 32) | L309G/M428L |
| EFc 6 (SEQ ID NO: 33) | P228L/V264M/L368Q/E388D/V422D/M428L/P445S |
| EFc 29 (SEQ ID NO: 34) | P228L/R292L/T359A/S364G/M428L |
| EFc 41 (SEQ ID NO: 35) | P228L/L234F/E269D/Q342L/E338D/T394A/M428L |
| EFc 82 (SEQ ID NO: 36) | P230Q/F243Y/K246E/N361S/N384I/M428L |
| EFc 88 (SEQ ID NO: 37) | P230S/Q295L/K320M/D356E/F405I/M428L |

Point mutations of the sorted variants

The positions of the mutations are numbered according to the Kabat EU numbering system, as described in Kabat et al., "Sequences of Proteins of Immunological Interest", 5th Ed., U.S. Department of Health and Human Services, NIH Publication No. 91-3242, 1991).

Example 5: Production and Purification of Control Trastuzumab for Introduction of the Fc Variants Trastuzumab (Herceptin®), a representative IgG1 therapeutic antibody, was selected as a control group. In the subsequent examples, the sorted Fc variants were introduced into trastuzumab.

Figure 6:
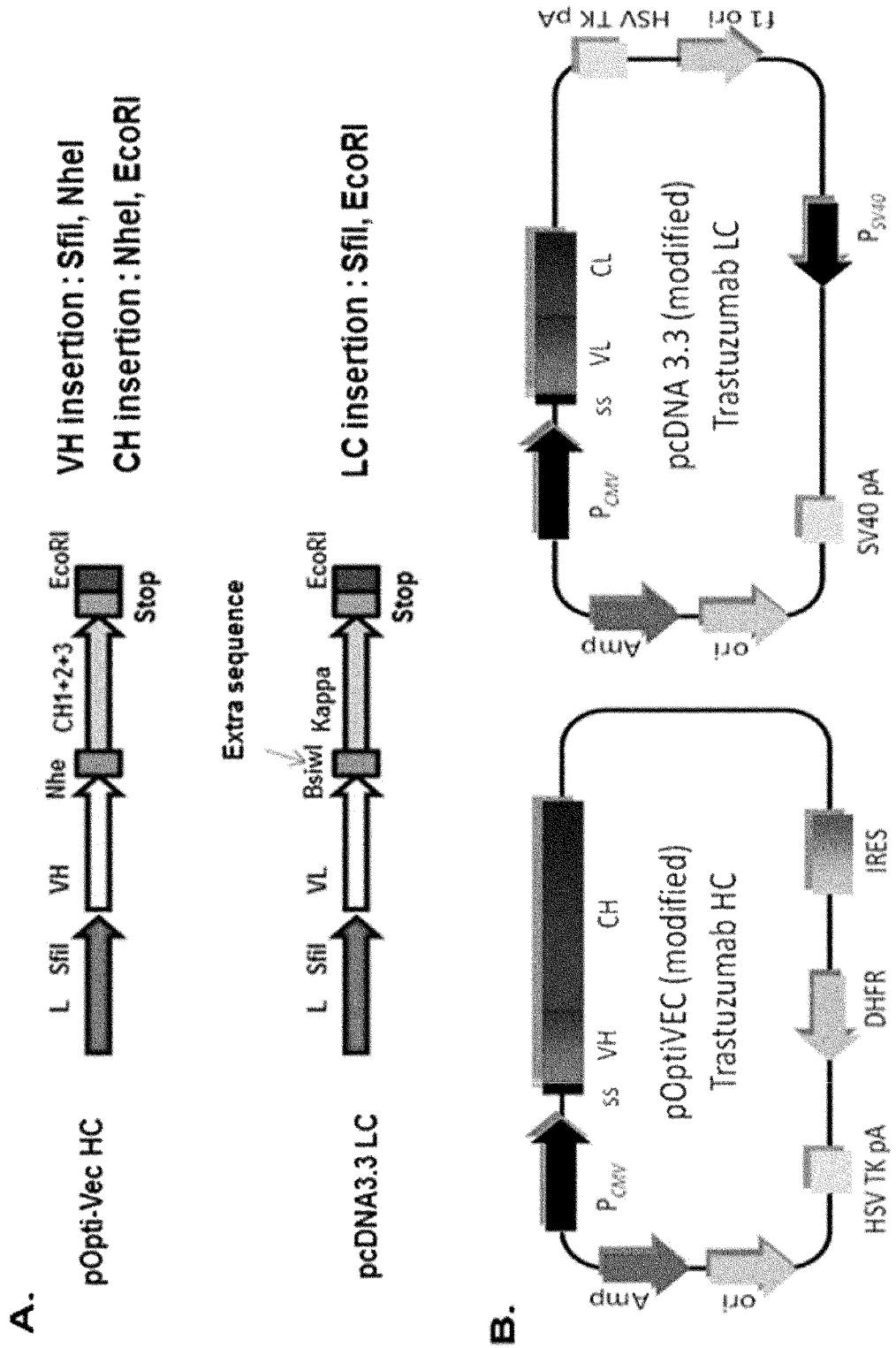
FIG. 6 shows plasmids for expressing trastuzumab heavy and light chains in animal cells.

The heavy and the light chain variable regions of wild-type trastuzumab were synthesized (Genscript) from the corresponding amino acid sequences from DrugBank Online (https://go.drugbank.com/) through mammalian codon optimization simultaneously with back-translation. The synthesized trastuzumab heavy and light chain genes were subcloned into pOptiVEC-Fc and pDNA3.3 vectors, respectively (FIG. 6). Animal cell expression plasmids encoding the trastuzumab heavy and light chains were prepared, expressed in HEK293 cells, and purified.

Figure 7:
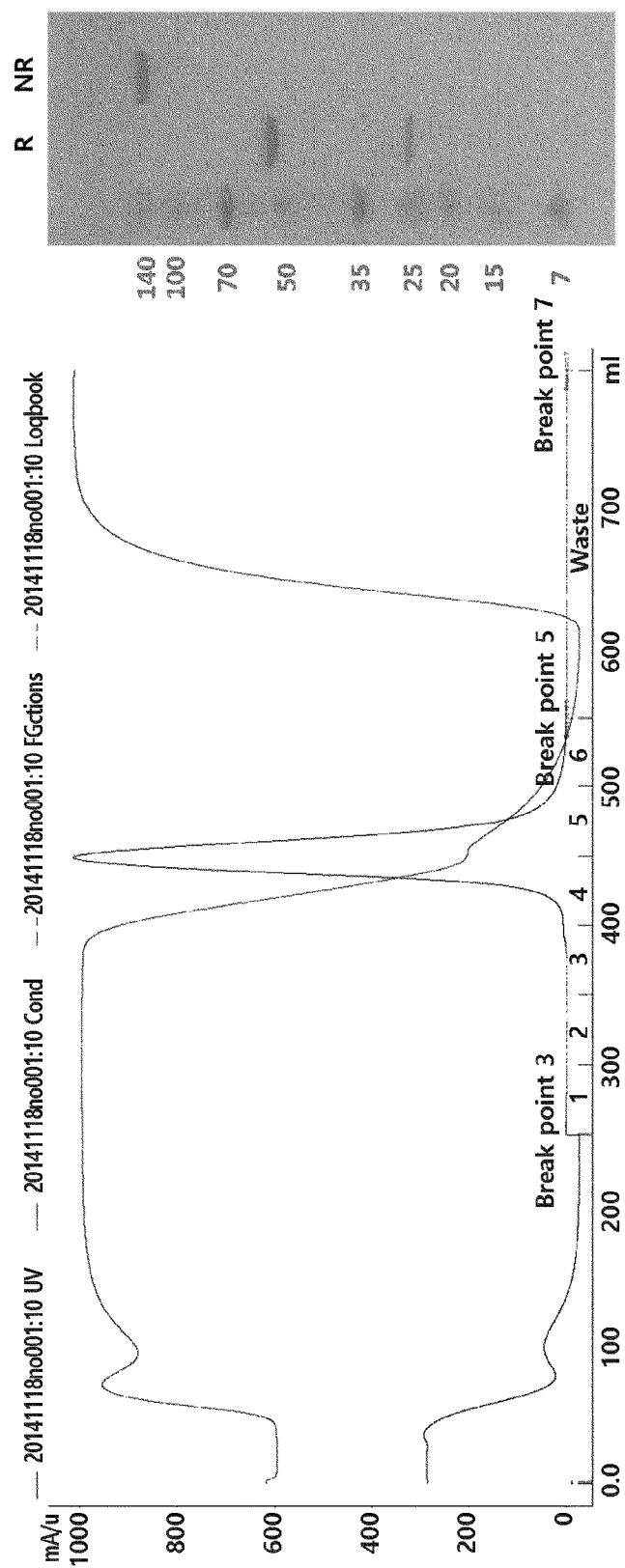
FIG. 7 shows expression and purification results for wild-type trastuzumab.

After culture in HEK 293F, the wild-type trastuzumab was purified by Protein A affinity chromatography (AKTA prime plus, cat #11001313) and gel permeation chromatography (HiTrap MabselectSure, GE, cat #11-0034-95). 7.7 mg of the wild-type trastuzumab was obtained in high purity from 300 ml of the culture medium (FIG. 7).

Figure 8B:
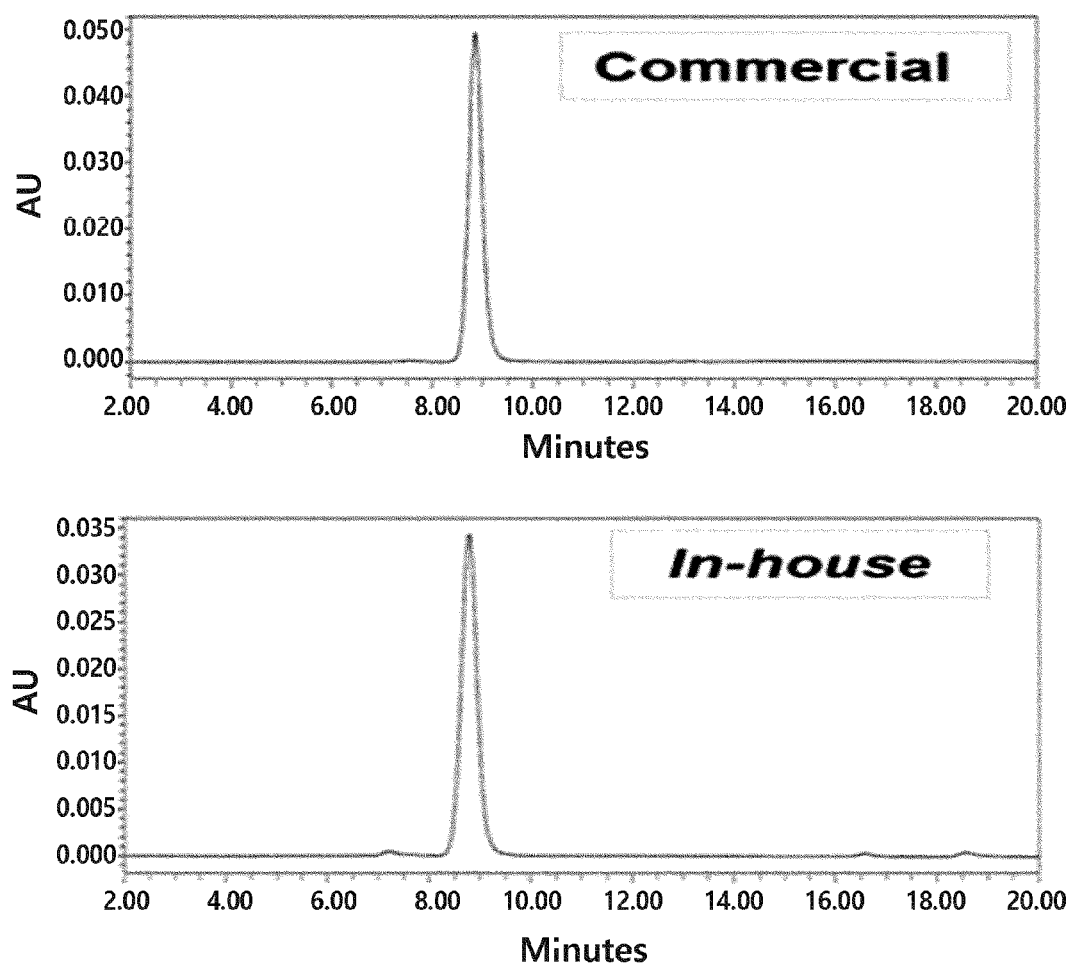
FIG. 8 compares the physical properties of commercial trastuzumab with those of in-house trastuzumab (a: CE-cIEF, b: SEC).
Figure 9A:
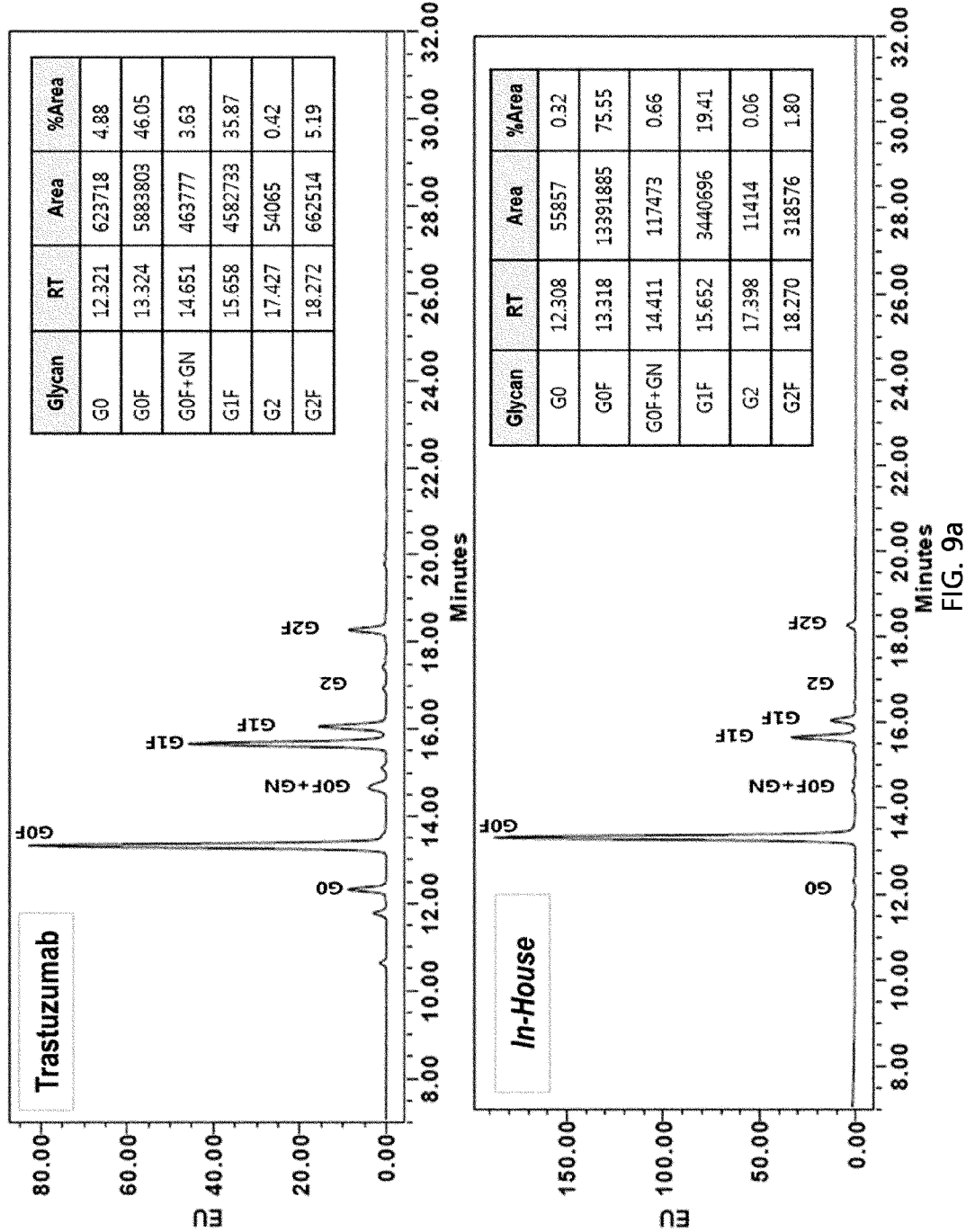
FIG. 9 compares the physical properties of commercial trastuzumab with those of in-house trastuzumab by N-glycan profiling.
Figure 9B:
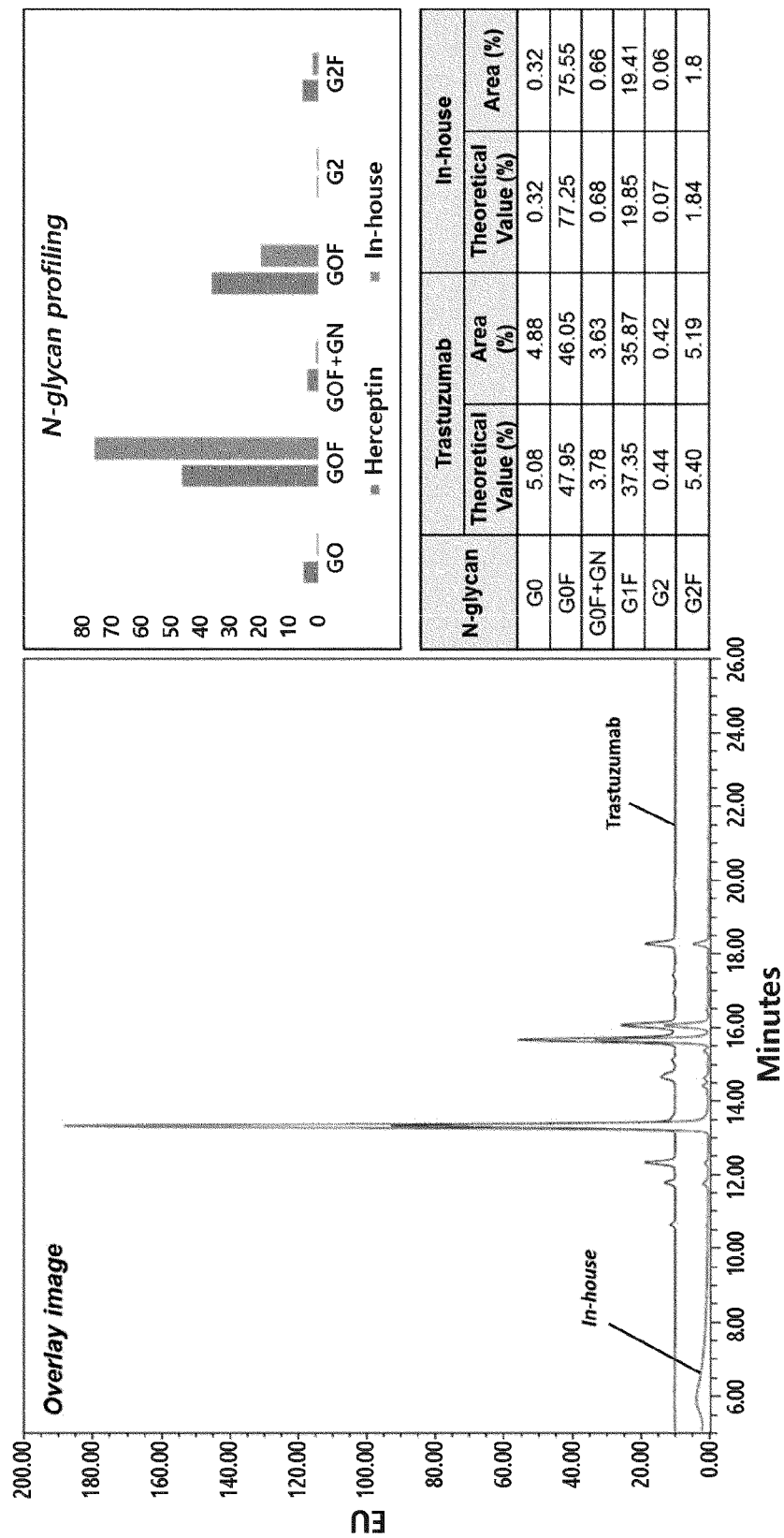

Example 6: Analysis and Comparison of Physical Properties of in-House Trastuzumab and Commercial Trastuzumab Unlike commercial trastuzumab produced by suspension culture in CHO cells, in-house trastuzumab was produced in HEK 293. Two basic characteristics of commercial trastuzumab and in-house trastuzumab antibodies were analyzed before introduction and function analysis of the sorted Fc variants. The pI values and charge variants of the samples were analyzed by capillary electrophoresis (CE: PA800 Plus, Beckman coulter) using Pharmalyte 3-10 carrier ampholytes (GE Healthcare, 17-0456-01) establishing a pH gradient of 3-10. The analytical results showed that no impurities were detected by size exclusion chromatography (SEC, Tskgel G3000swxl, Tosoh). For the commercial trastuzumab, the pI values by charge variants were 8.27-8.74 and the pI of the main peak was 8.62. For the in-house trastuzumab, the pI values by charge variants were 8.29-8.78 and the pI of the main peak was 8.65, which were almost the same as those for the commercial trastuzumab (FIG. 8). The pI values were measured by capillary electrophoresis (CE, PA800 Plus, Beckman coulter). However, cIEF analysis revealed that there were slight differences in the content of the in-house trastuzumab at the main peak and the other peaks. These differences are because of the different glycan patterns of the in-house trastuzumab produced in HEK293 cell line and the commercial trastuzumab produced in CHO cell line, leaving a possibility that the in-house trastuzumab might be oxidized by sialic acid. Thus, glycan analysis was also performed (FIG. 9).

After cleavage of N-glycan from the protein with PNGase F (NEB, 186007990-1) and labeling with RapiFluor-MS reagent (Waters, 186007989-1), glycan analysis was performed using a UPLC system (Acquity UPLC I class, Waters, FLR detector). As a result of the glycan analysis, the glycan patterns were similar but different glycan contents of the compositions were observed, which seems to be not caused by sialic acid-induced oxidation but by the different production cell lines. Further, glycans were found top have no significant influence on binding force analysis and pharmacokinetic analysis (data not shown). Thus, the sorted Fc variants were introduced into the commercial trastuzumab and the in-house trastuzumab.

Example 7: Production and Purification of the Fc Variants and Analysis of Physical Properties of the Fc Variants Five control variants, including the commercial wild-type variant, the in-house wild-type variant, LS (XenCor), YTE (MedImmune), and 428L, and the sorted variants PFc29, PFc41, EFc29, EFc41, and EFc82 were transfected into HEK 293F animal cells. On the day before transfection, 300 ml of HEK293F cells were passaged at a density of $1\times10^6$ cells/ml. On the next day, cells were transfected with polyethylenimine (PEI, Polyscience, 23966). First, a heavy chain gene and a light chain gene of each of the variants were mixed in a 2:1 ratio in 30 ml of Freestyle 293 expression culture medium (Gibco, 12338-018). Then, PEI and the variant genes were mixed in a 1:2 ratio, left standing at room temperature for 20 min, mixed with the cells that had been passaged on the previous day, cultured in a C02 shaking incubator at 125 rpm, 37° C., and 8% C02 for 6 days, and centrifuged. The supernatant only was collected.

Figure 10A:
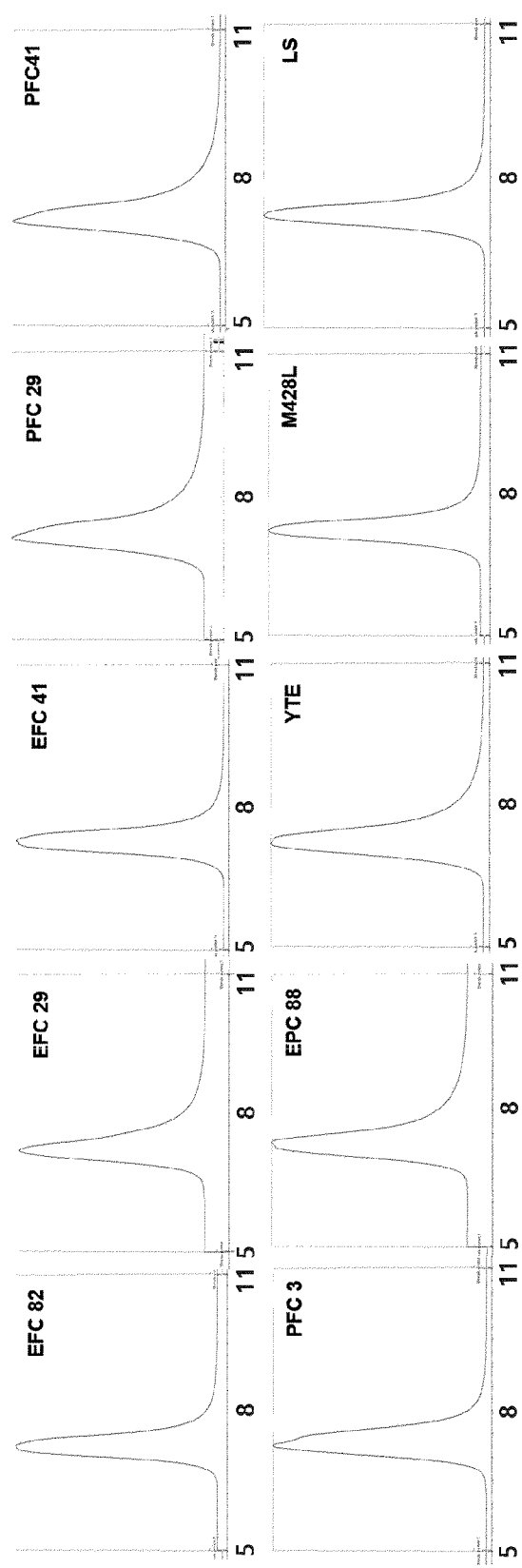
FIG. 10 shows expression and purification results for 10 trastuzumab Fc variants (a: affinity chromatography, b: SDS-PAGE analysis, c: list of final yield).
Figure 10B:
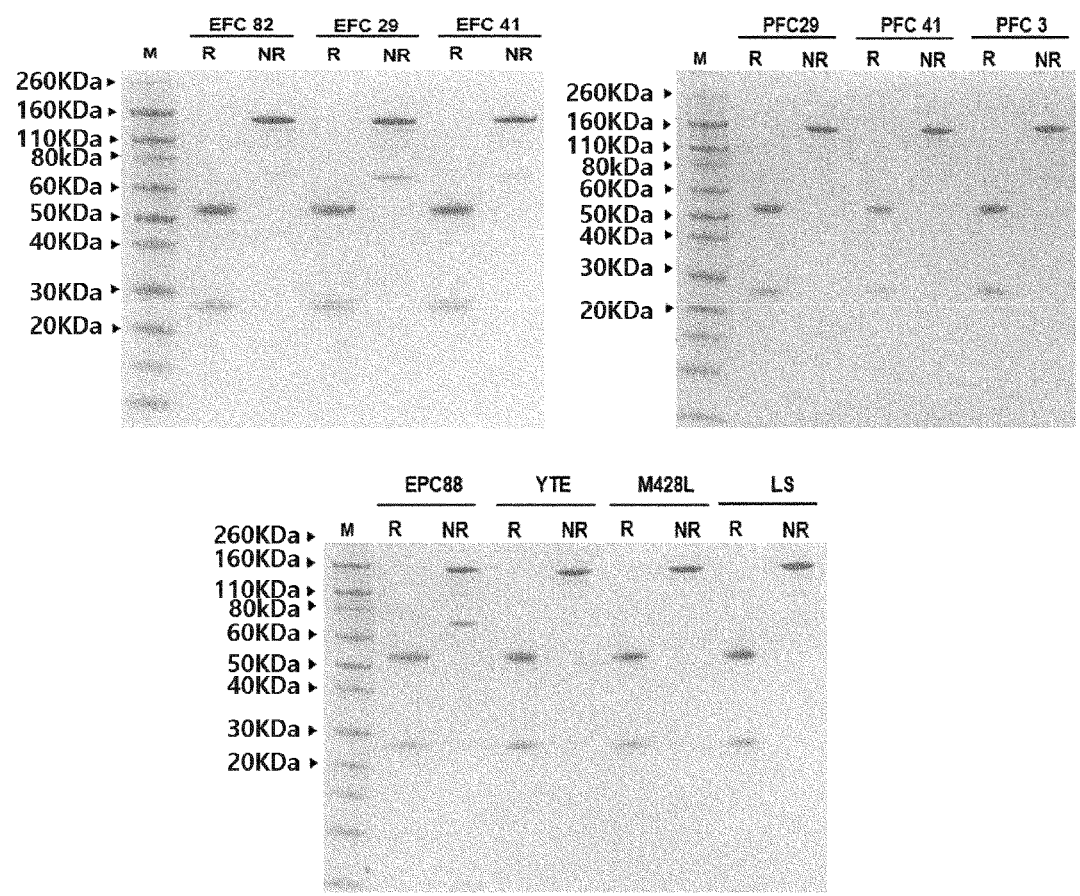
Figure 11A:
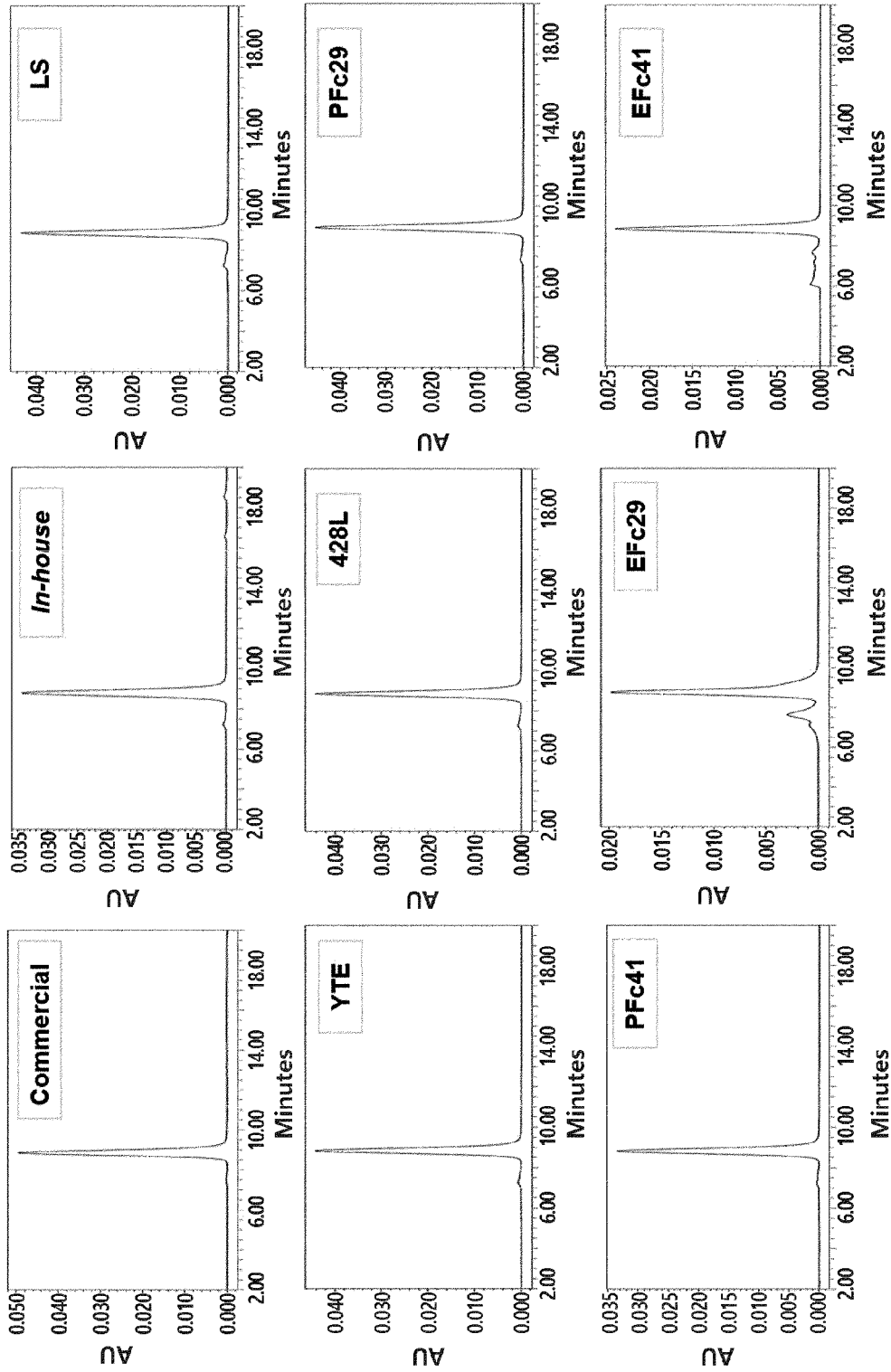
FIG. 11 shows SEC characterization results for trastuzumab Fc variants.

The proteins were purified from the supernatant by affinity chromatography using AKTA prime plus with a HiTrap MabselectSure column. 300 ml of the supernatant was allowed to flow through the column at a rate of 3 ml/min and washed with 100 ml of 1×PBS. Then, IgG Elution buffer (Thermo scientific, 21009) was allowed to flow through the column at a rate of 5 ml/min. Six fractions (5 ml each) were collected. Each fraction was neutralized with 500 µl of 1M Tris (pH 9.0). The fraction was determined for proteins using Bradford (BioRad, 5000001) and put in a new tube. The purified variants were concentrated using a 30K Amicon ultra centrifugal filter (UFC903096) and their physical properties were analyzed (FIGS. 10 and 11).

Figure 11B:
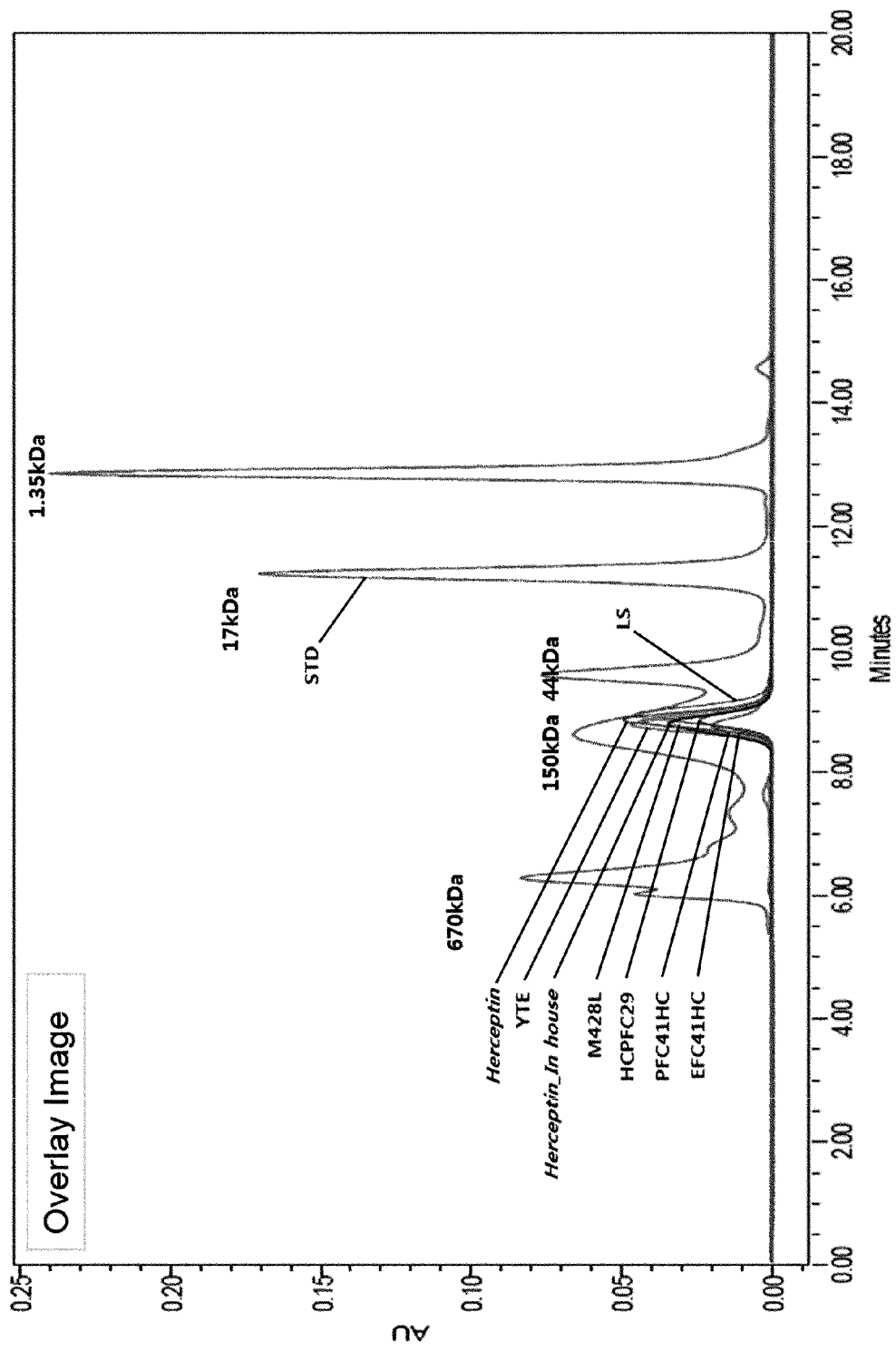
Figure 12A:
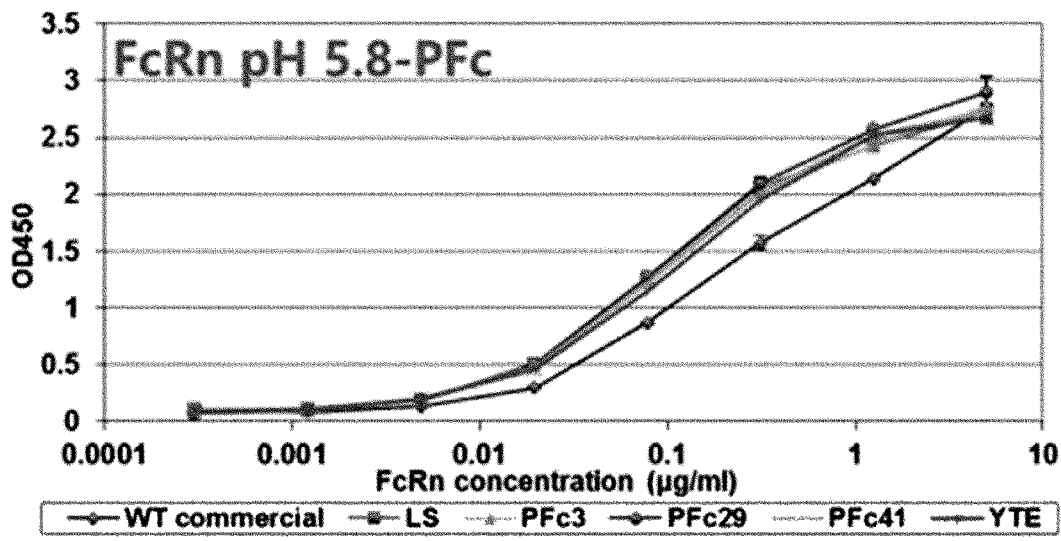
FIG. 12 shows binding forces of trastuzumab Fc variants to FcRn, which were measured by ELISA.
Figure 12B:
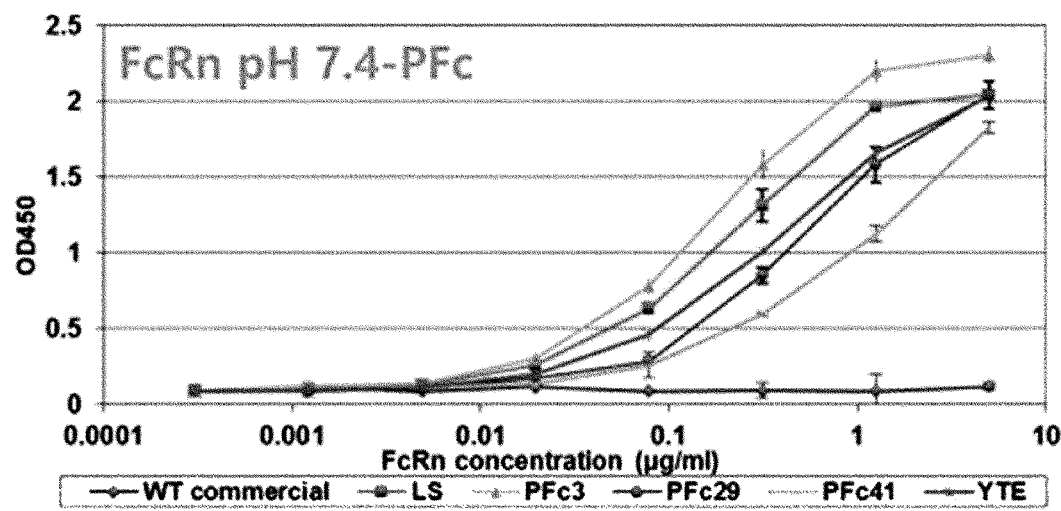
Figure 12C:
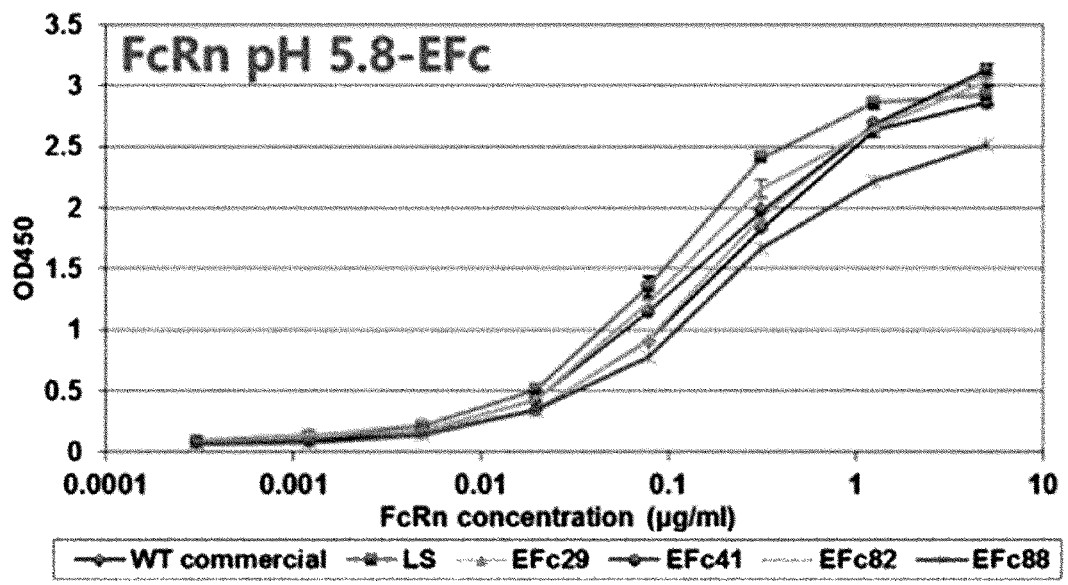
Figure 12D:
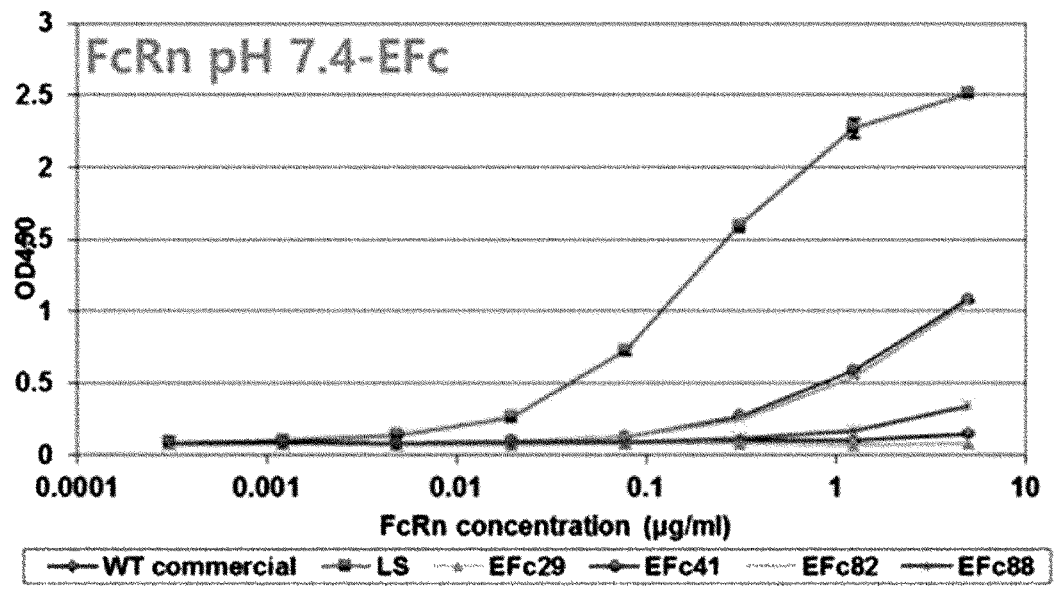

Each of the Fc variants other than the in-house wild-type trastuzumab was purified with protein A and its purity (>90%) and molecular weight were determined by SDS-PAGE. SEC-HPLC (FIG. 11a) was used to obtain high-purity protein samples for efficacy evaluation and purity analysis (purity ≥97%). Analysis under isocratic conditions (mobile phase 1×PBS, pH 7.0, 1 ml/min flow rate) revealed that all Fc variants had the same retention time for the main peaks and had estimated molecular weights (FIG. 11b).

Example 8: Measurement of Binding Forces of the Fc Variants to FcRn by ELISA

ELISA was conducted to measure the pH-dependent binding forces of the prepared variants to FcRn and the binding forces of the variants to FcγRs and C1q, which allow the variants to exhibit effector functions. First, the pH-dependent binding forces of the variants to FcRn were investigated. To this end, 50 µl of each of the IgG Fc variants diluted to 4 µg/ml with 0.05 M $Na_2CO_3$ (pH 9.6) was immobilized onto a flat-bottom polystyrene high-bind 96-well microplate (costar) at 4° C. for 16 h, blocked with 100 µl of 4% skim milk (GenomicBase) (in 0.05% PBST pH 5.8/pH 7.4) at room temperature for 2 h, and washed four times with 180 µl of 0.05% PBST (pH 5.8/pH 7.4). Thereafter, 50 µl of FcRn serially diluted with 1% skim milk (in 0.05% PBST pH 5.8/pH 7.4) was plated in each well and the reaction was carried out at room temperature for 1 h. After washing, an antibody reaction with 50 µl of anti-GST-HRP conjugate (GE Healthcare) was allowed to proceed at room temperature for 1 h. The plate was washed and developed with 50 µl of 1-Step Ultra TMB-ELISA Substrate Solution (Thermo Fisher Scientific). The reaction was quenched with 2 M $H_2SO_4$ (50 µl each). Then, the reaction product was analyzed using an epoch microplate spectrophotometer (BioTek). The sorted variants had binding forces to FcRn at pH 5.8 similar to the variant LS and were more easily dissociated at pH 7.4 than LS (FIG. 12).

Example 9: Measurement and Comparison of Binding Forces of the Trastuzumab Fc Variants to Monomeric hFcRn at pH 6.0 and pH 7.4

Figure 13B:
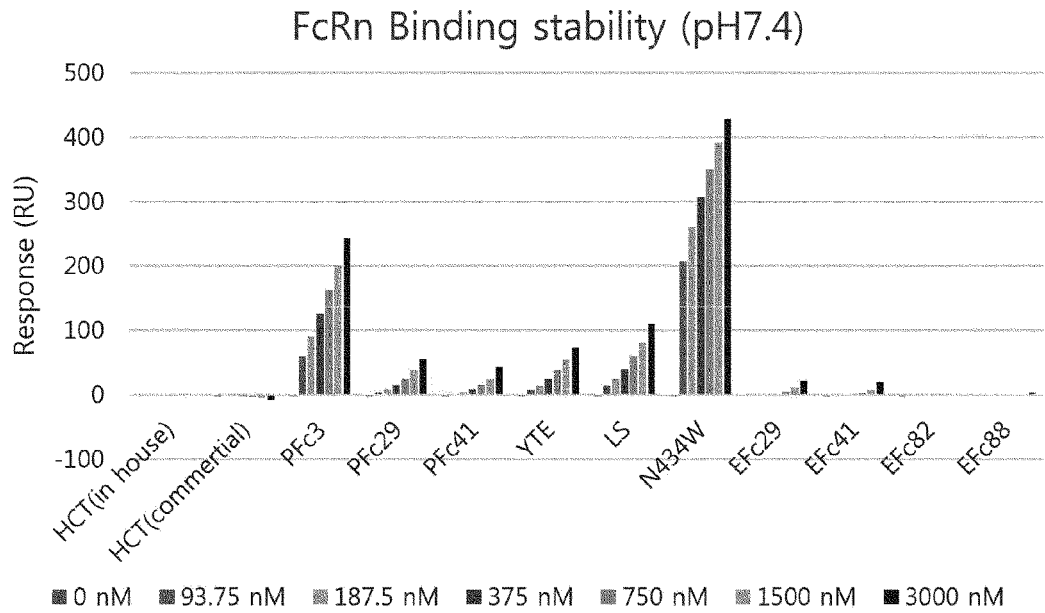
FIG. 13 shows binding forces of trastuzumab Fc variants to hFcRn at pH values of 6.0 and 7.4, which were measured using a BiaCore instrument (a: pH 6.0 (capture method) b: pH 7.4 (avid format)).
Figure 13B:
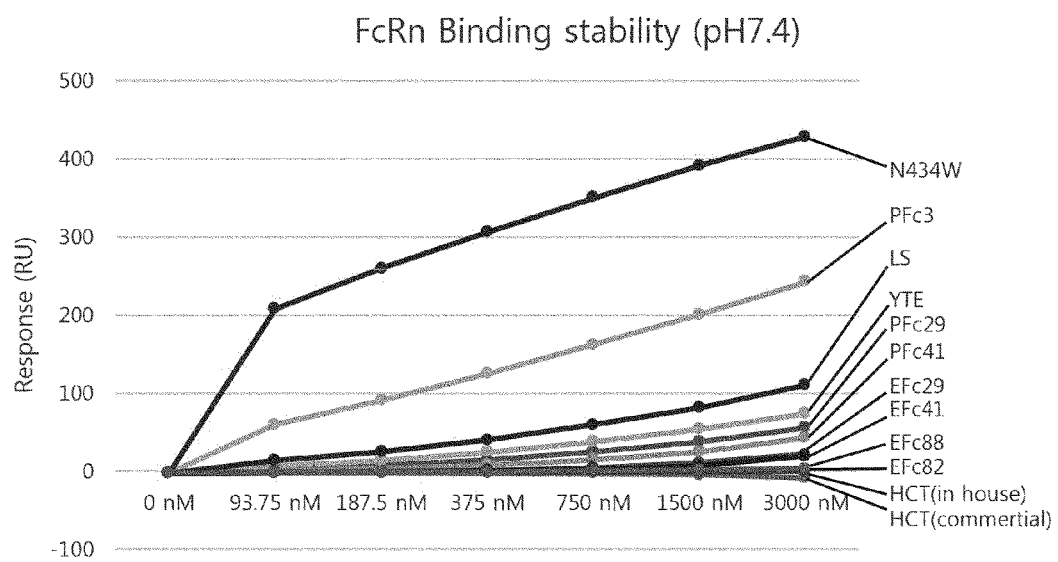

In this example, the pH-dependent binding forces of the commercial trastuzumab, the in-house trastuzumab, and the sorted Fc variants, which were analyzed and investigated for physical properties, to human FcRn were compared. Specifically, $K_D$ values were measured using a Biacore T200 instrument (GE Healthcare). At pH 6.0, human FcRn was used as an analyte in an antigen-mediated antibody capture format, as disclosed in the literature (Yeung Y A. et al., *J. Immunol*, 2009). Each Fc variant as a ligand was diluted in running buffer (50 mM phosphate, pH 6.0, 150 mM NaCl, 0.005% surfactant P20, pH 6.0), injected at a level of ~300 response units (RUs) into the surface of CM5 chip on which HER2 ECD domain was immobilized to a level of ~3,000 RUs, and captured. For binding force measurement, monomeric FcRn (Sinobiological inc., CT009-H08H) as an analyte was serially diluted from 125 nM in FcRn running buffer, injected at a flow rate of 30 µl/min for 2 min, followed by dissociation for 2 min. In each cycle, regeneration was performed with 10 mM glycine (pH 1.5) at a flow rate of 30 ml/min for 30 sec. Sensograms were fit to a 1:1 binding model using the BIAevaluation software (Biacore). As a result, the Fc variants had higher binding forces (PFc 3: 5.6 nM, PFc29: 6.8 nM, PFc 41: 5.9 nM, etc.) than the commercial trastuzumab (15 nM) and the in-house trastuzumab (16.9 nM) as control groups and 428L (9 nM) as the backbone. However, the Fc variants had rather lower binding forces than YTE (5.7 nM) and LS (4.1 nM) whose binding forces are known to be the highest values in the world, but their differences were almost the same within the error range. Since the ligands were less bound to the analyte at pH 7.0, dissociation was evaluated using an avid format in which monomeric hFcRn was directly immobilized and different concentrations of the Fc variants were injected (Zalevsky J et al. *Nat. Biotechnol*, 2010). Human FcRn ECD domain (Sino Biological) was immobilized to a level of ~1,500 RUs onto the surface of a CM5 chip. The Fc variants were serially diluted from 3000 nM in HBS-EP (pH 7.4) and injected at a flow rate of 5 ml/min into the FcRn-immobilized chip surface for 2 min. The bound Fc variants were dissociated for 2 min. After each cycle was finished, the chip surface was regenerated with 100 mM Tris (pH 9.0) (conatat time 30 sec; flow rate 30 l/min). Particularly, the Fc variants PFc29 and PFc41 maintained their high binding forces at pH 6.0 and were more rapidly dissociated at pH 7.4 than YTE and LS. These results were in agreement with the results obtained by ELISA and suggest long expected half-lives of the Fa variants (FIG. 13). In practice, in vivo pharmacokinetic experiments were conducted in human FcRn Tg mice.

Figure 14:
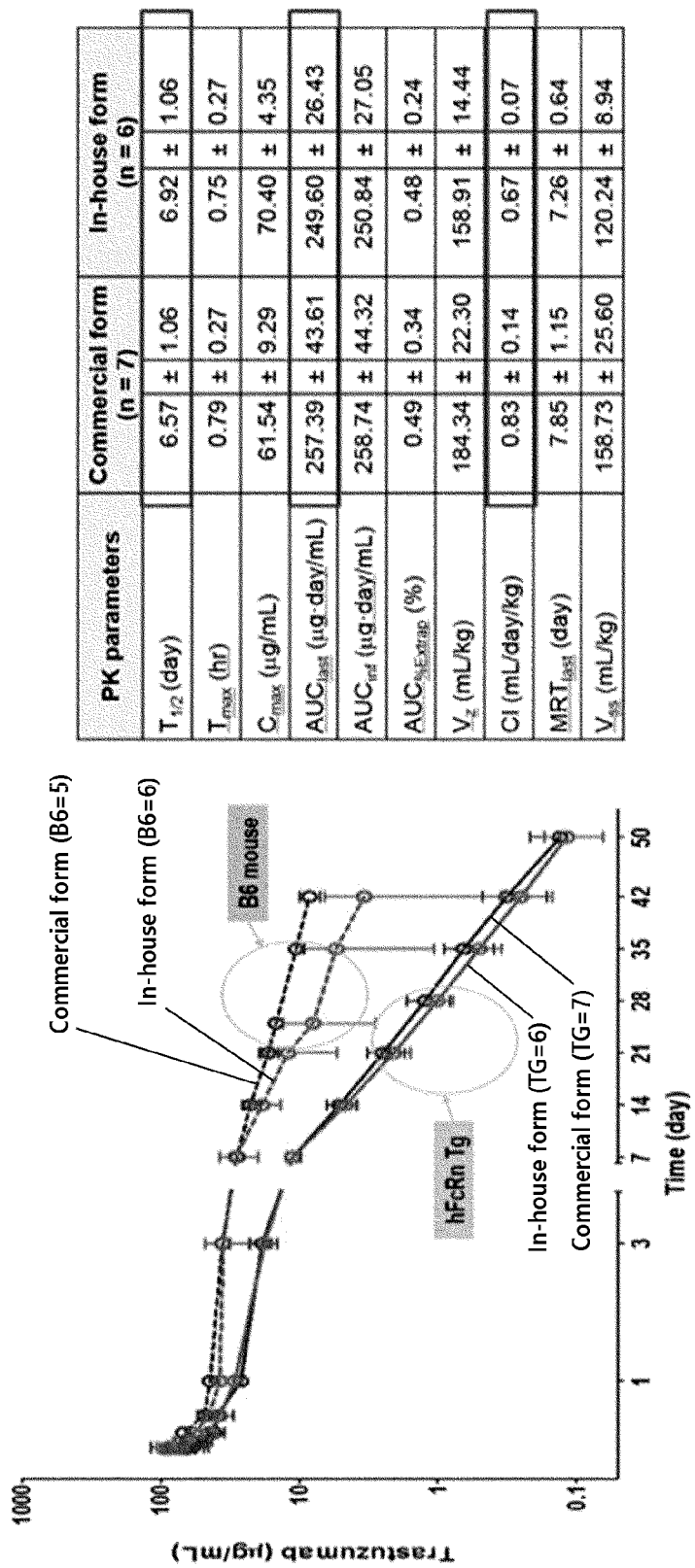
FIG. 14 compares the pharmacokinetics of commercial trastuzumab with those of in-house trastuzumab in regular mice (C57BL/6J (B6)) and human FcRn Tg mice.

Example 10: Analysis and Comparison of In Vivo PK Experiments of the Commercial Trastuzumab and the in-House Trastuzumab in Regular B6 Mice and hFcRn Tg Mice PK analysis was conducted on regular B6 mice (Jungang Experimental Animal Resource Center, C57BL/6J(B6)) whose genetic background is identical to that of human FcRn Tg mice. As a result, the affinity of the Fc of a human antibody for regular mouse FcRn was found to be higher than that for human FcRn, as reported in the literature. There was a variation in the PK values between the in-house antibody and the commercial antibody in the regular mice, and the in-house antibody appeared to be unstable. Further, the AUC in the Tg mice (B6.Cg-Fcgrttm1Dcr Prkdcscid Tg (Jackson lab, CAGFCGRT)276Dcr/DcrJ) was slightly lower than that in the regular mice but the in-house antibody and the commercial antibody showed similar pharmacokinetic tendencies. demonstrating that no problems were encountered in experiments using the in-house Fc variants produced in HEK293 to analyze the actual in vivo pharmacokinetics of the Fc variants in the Tg mice (FIG. 14).

Figure 15:
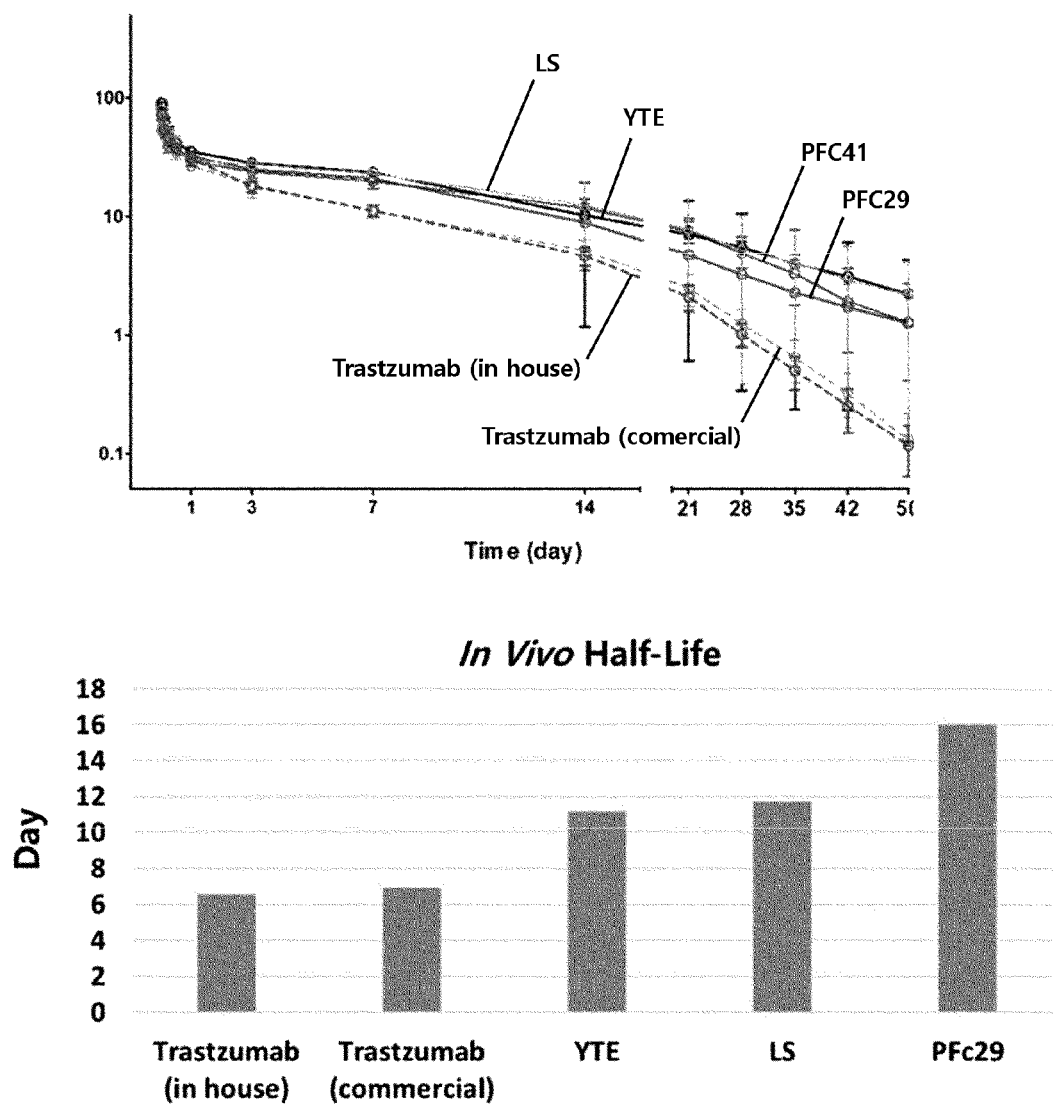
FIG. 15 shows the results of pharmacokinetic analysis for Fc variants in human FcRn Tg mice (after intravenous injection of the variants (5 mg/kg each), n=5).
Figure 16A:
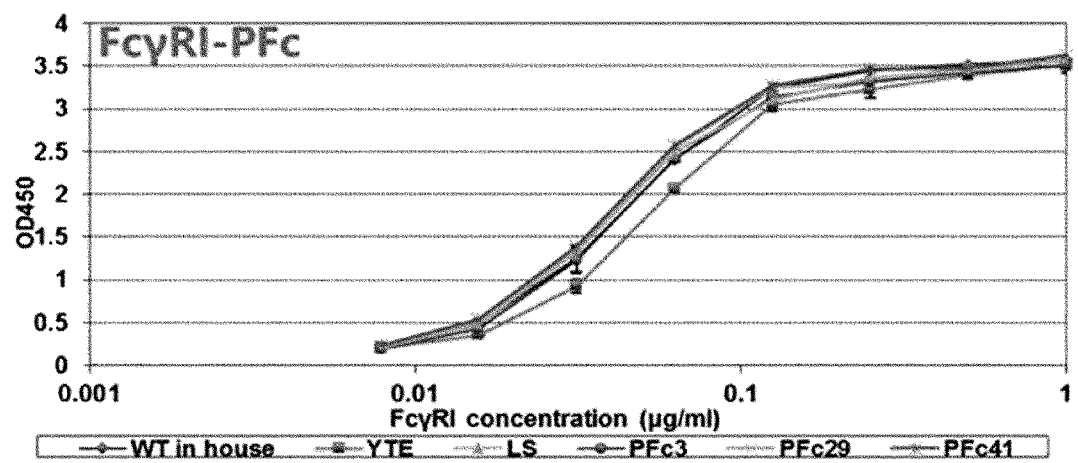
FIG. 16 shows binding forces of trastuzumab Fc variants to FcγRs, which were measured by ELISA.
Figure 16B:
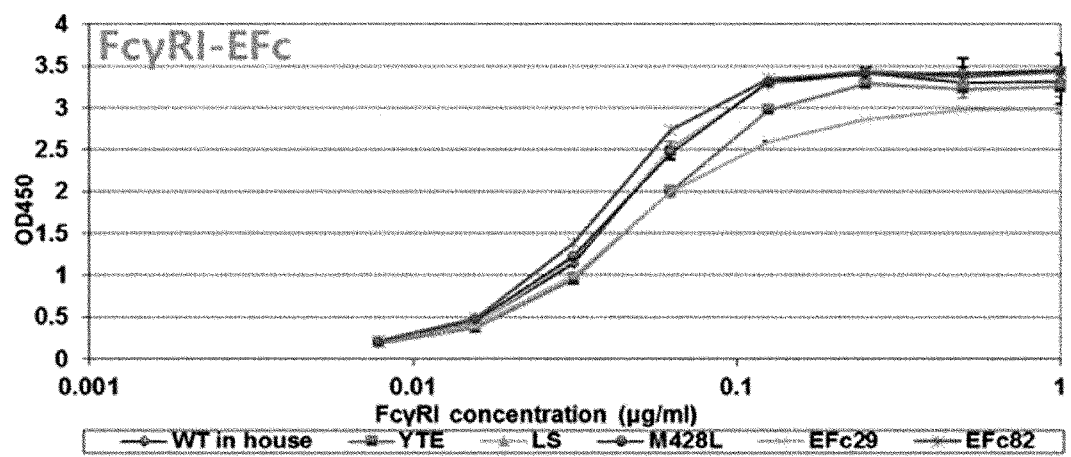
Figure 16C:
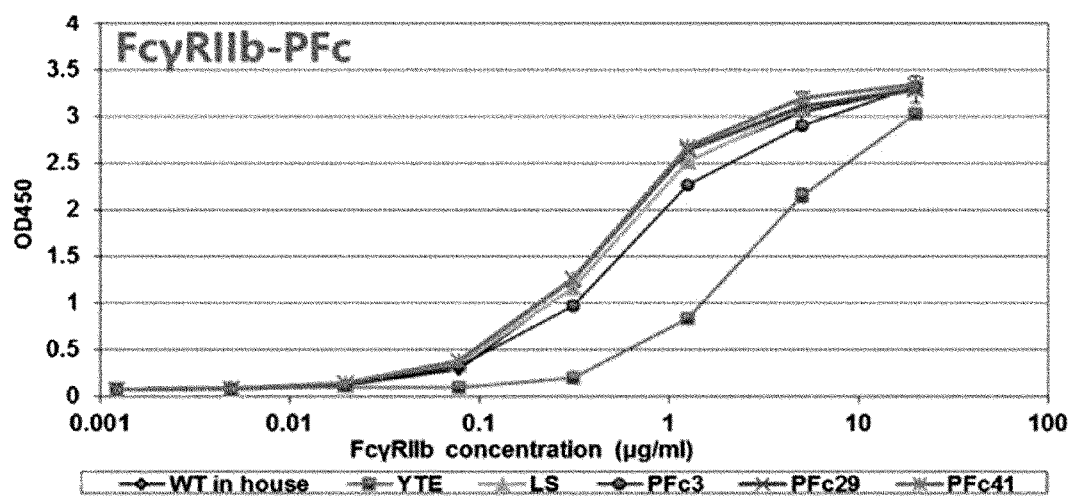
Figure 16D:
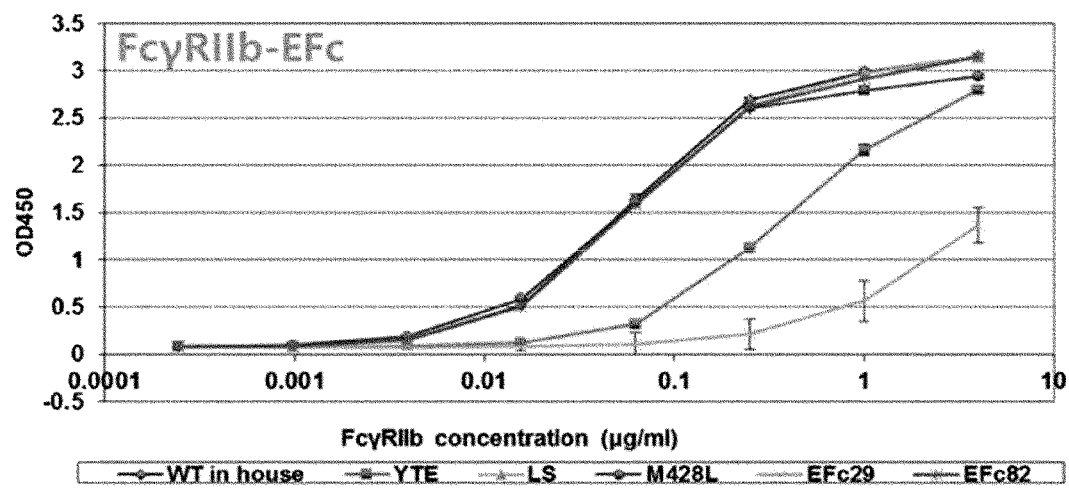
Figure 16E:
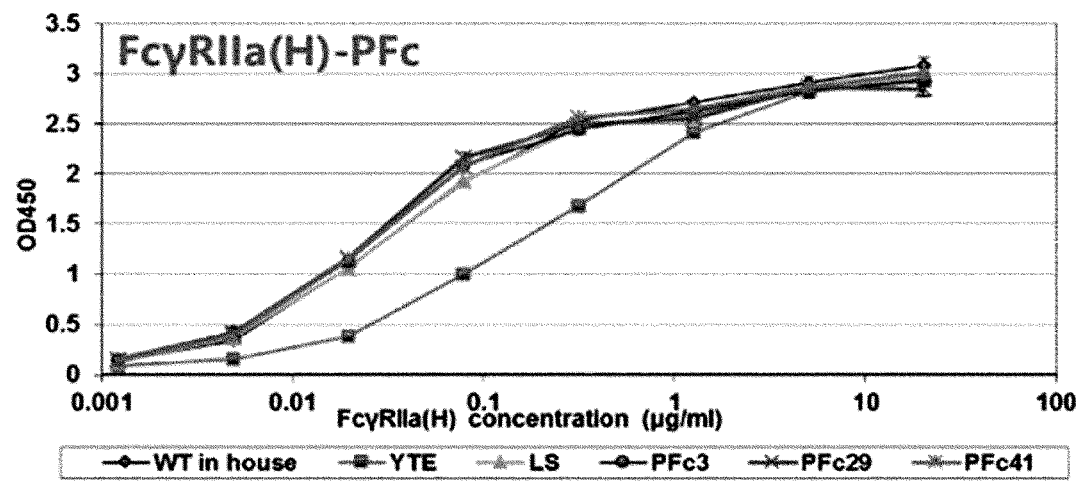
Figure 16F:
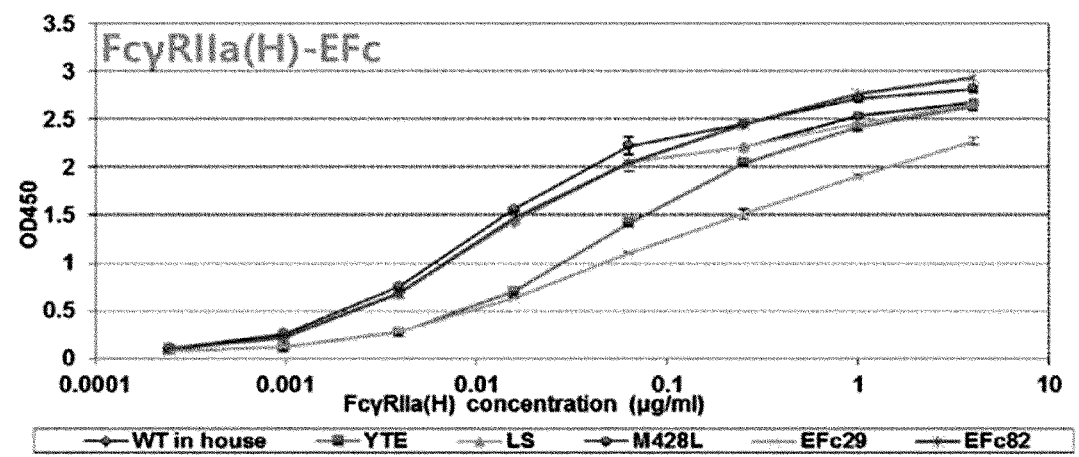
Figure 16G:
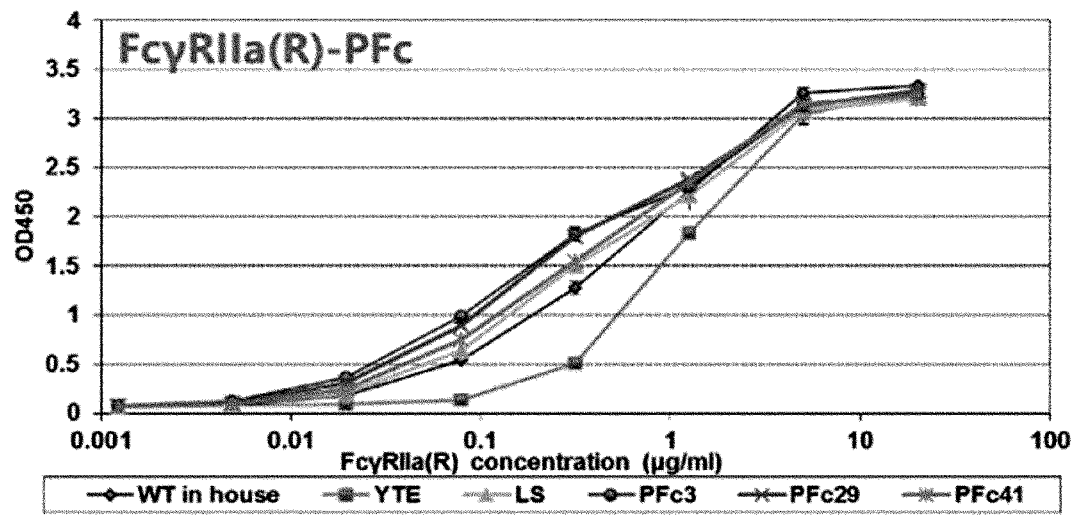
Figure 16H:
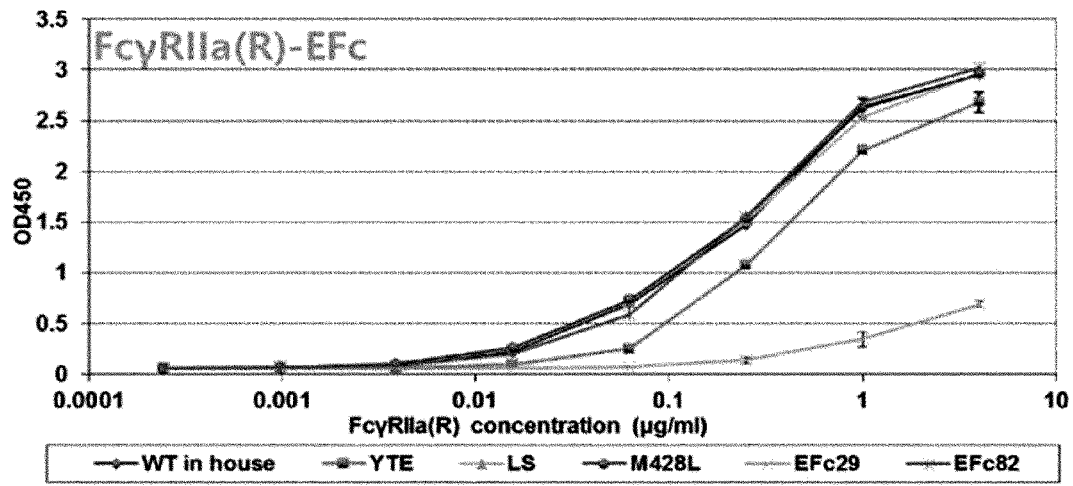
Figure 16I:
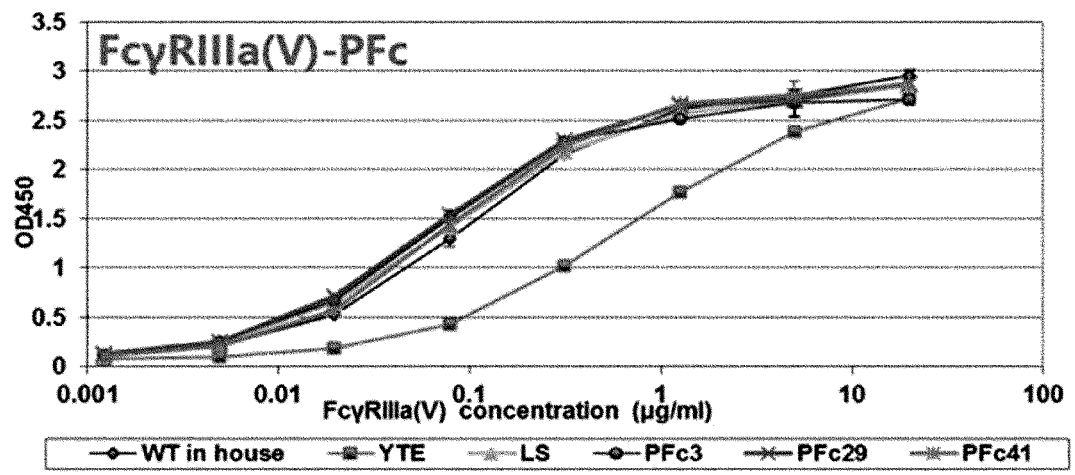
Figure 16J:
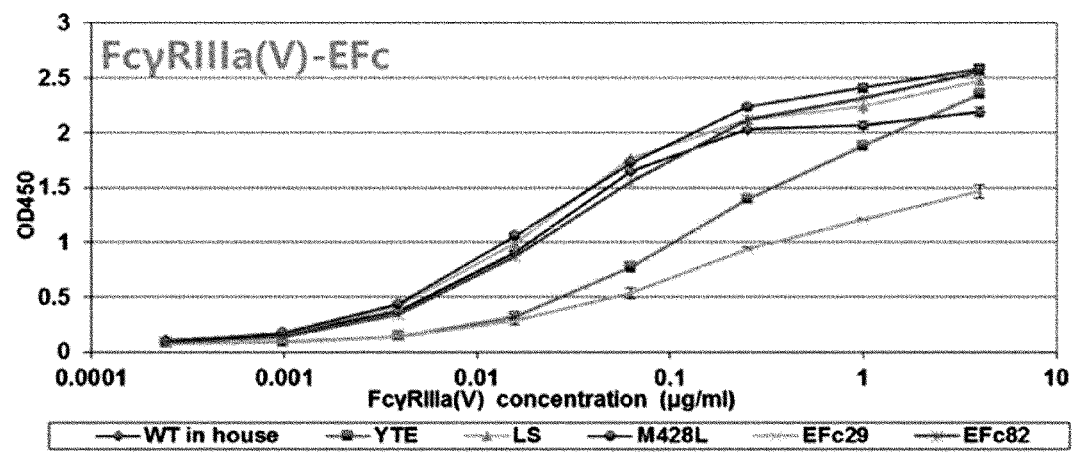
Figure 16K:
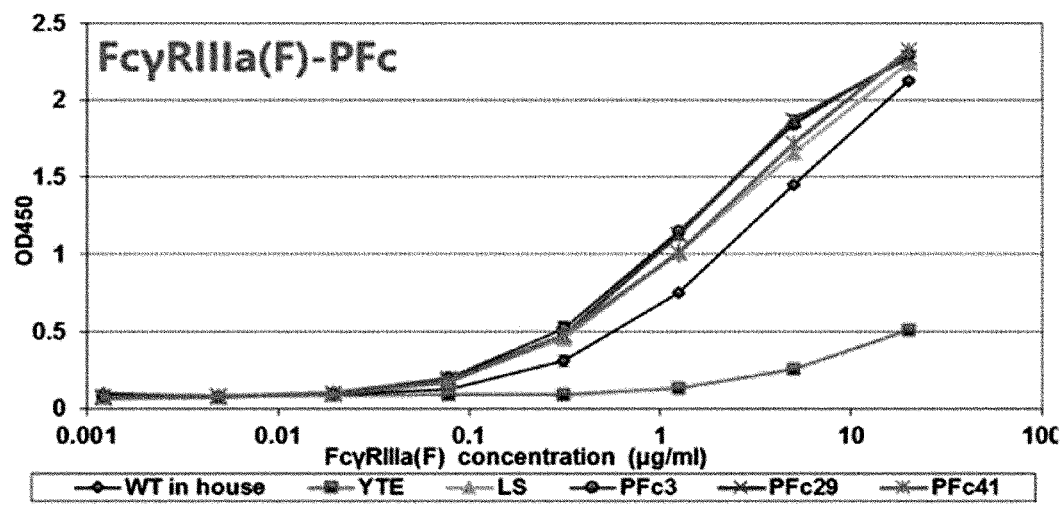
Figure 16L:
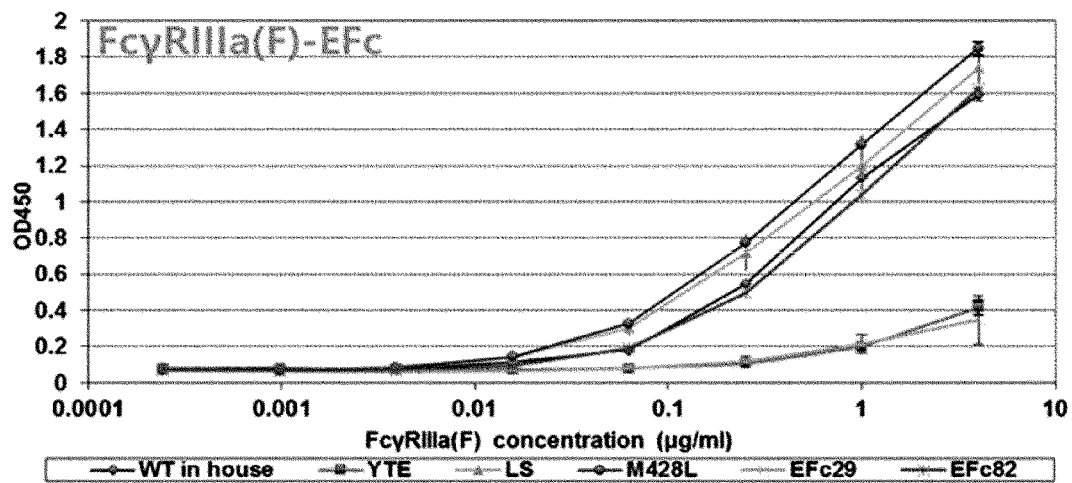

Example 11: Pharmacokinetics of Four Species, Including LS, YTE, and Variants PFc29 and PFc41 in hFcRn Tg Mice The binding forces measured at pH 6.0 and pH 7.4 using an ELISA system and a BiaCore instrument were found to be constant. Based on these results, PFc29 and PFc41 were sorted due to their high binding forces comparable to that of LS under acidic conditions (pH 6.0) and higher dissociation forces at pH 7.4 than that of LS. Simultaneously with this, LS mutant from Xencor and YTE from MedImmune as control groups, which are currently known to be most effective in the world, and the two trastuzumab Fc variants were injected into 20 human FcRn Tg mice (5 animals per group, 5 mg/kg I.V (tail vein)). After injection, blood samples were collected a total of 12 times (0, 30 min, 1 hr, 6 hr, 24 hr, 3 day, 7 day, 14 day, 21 day, 28 day, 35 day, 42 day, and 50 day) from the facial vein. The concentrations of the Fc variants in the blood samples were analyzed by ELISA and then non-compartmental analysis (NCA) was conducted using WinNonlin. As expected from the results of ELISA and BiaCore analysis, the Fc variants PFc29 and PFc41 showed increased in vivo half-lives. Particularly, the half-life of PFc29 was longer than that of conventional LS (FIG. 15 and Table 3).

Example 13: Measurement of Effector Functions of the Fc Variants by Antibody-Dependent Cell-Mediated Cytotoxicity (ADCC)

The antibody-dependent cellular cytotoxicity (ADCC) activities of the trastuzumab Fc variants were evaluated using an ADCC reporter bioassay kit (Promega, G7010). Specifically, SKBR-3 cells as target cells were plated at a density of $5\times10^3$ cells/100 μl in each well of a 96-well tissue culture plate and cultured in a C02 incubator at 37° C. for 20 h. Thereafter, 95 μl of the culture medium was removed from each well of the plate using a multi-pipette and 25 μl of ADCC assay buffer provided from the ADCC reporter bioassay kit was plated in each well. Normal IgG, trastuzumab, and the trastuzumab Fc variants were diluted to various concentrations with ADCC assay buffer. 25 μl of each dilution was plated in each well of the 96-well tissue culture plate containing the cells and left standing at room temperature until effector cells were added. Effector cells

TABLE 3

| Parameter | PFc29 | PFc41 | YTE | LS | Trastuzumab (in-house) | Trastuzumab (commercial) |
|---|---|---|---|---|---|---|
| $t_{1/2}$ (day) | 15.99 ± 9.57 | 10.87 ± 3.77 | 11.16 ± 7.21 | 11.72 ± 7.20 | 6.92 ± 1.06 | 6.57 ± 1.06 |
| $T_{max}$ (h) | 0.70 ± 0.27 | 0.70 ± 0.27 | 0.70 ± 0.27 | 0.70 ± 0.27 | 0.75 ± 0.27 | 0.79 ± 0.27 |
| $C_0$ (μg/mL) | 85.11 ± 11.31 | 69.72 ± 11.42 | 89.26 ± 12.54 | 82.72 ± 8.18 | 75.60 ± 4.11 | 64.98 ± 40.08 |
| $C_{max}$ (μg/mL) | 78.19 ± 9.55 | 65.22 ± 10.60 | 82.55 ± 11.36 | 75.92 ± 7.07 | 70.40 ± 4.35 | 61.54 ± 9.29 |
| $AUC_{last}$ (μg/mLxday) | 418.30 ± 120.22 | 466.04 ± 51.57 | 520.26 ± 214.61 | 522.25 ± 182.53 | 249.60 ± 26.43 | 257.39 ± 43.61 |
| $AUC_{inf}$ (μg/mLxday) | 450.03 ± 158.08 | 489.92 ± 68.62 | 574.14 ± 264.60 | 574.95 ± 228.28 | 250.84 ± 27.05 | 258.74 ± 44.32 |
| $AUC_{\%Extrap}$ (%) | 5.36 ± 6.20 | 4.55 ± 3.33 | 6.86 ± 6.57 | 7.24 ± 6.73 | 0.48 ± 0.24 | 0.49 ± 0.34 |
| $V_z$ (mL/kg) | 292.54 ± 271.40 | 157.05 ± 41.29 | 126.70 ± 39.27 | 135.94 ± 52.09 | 158.91 ± 14.44 | 184.34 ± 22.30 |
| CL (mL/day/kg) | 12.29 ± 4.31 | 10.36 ± 1.41 | 10.91 ± 5.96 | 10.21 ± 4.92 | 0.67 ± 0.07 | 0.83 ± 0.14 |

Non-compartmental analysis of pharmacokinetic parameters of trastuzumab Fc variants after intravenous administration (5 mg/kg) to mice (data are expressed as mean ±SD (n = 5)).
$t_{1/2}$, terminal half-life;
$T_{max}$, time at maximal concentration;
$C_0$, extrapolated zero time concentration;
$C_{max}$, maximal concenration,
$AUC_{last}$, area under the curve from administration to the last measured concentration;
$AUC_{inf}$, area under the curve from administration to infinity;
$AUC_{\%Extrap}$, percentage of the extrapolated area under the curve at the total area under the curve;
$V_z$, volume of distribution;
CL, clearance.

Figure 17:
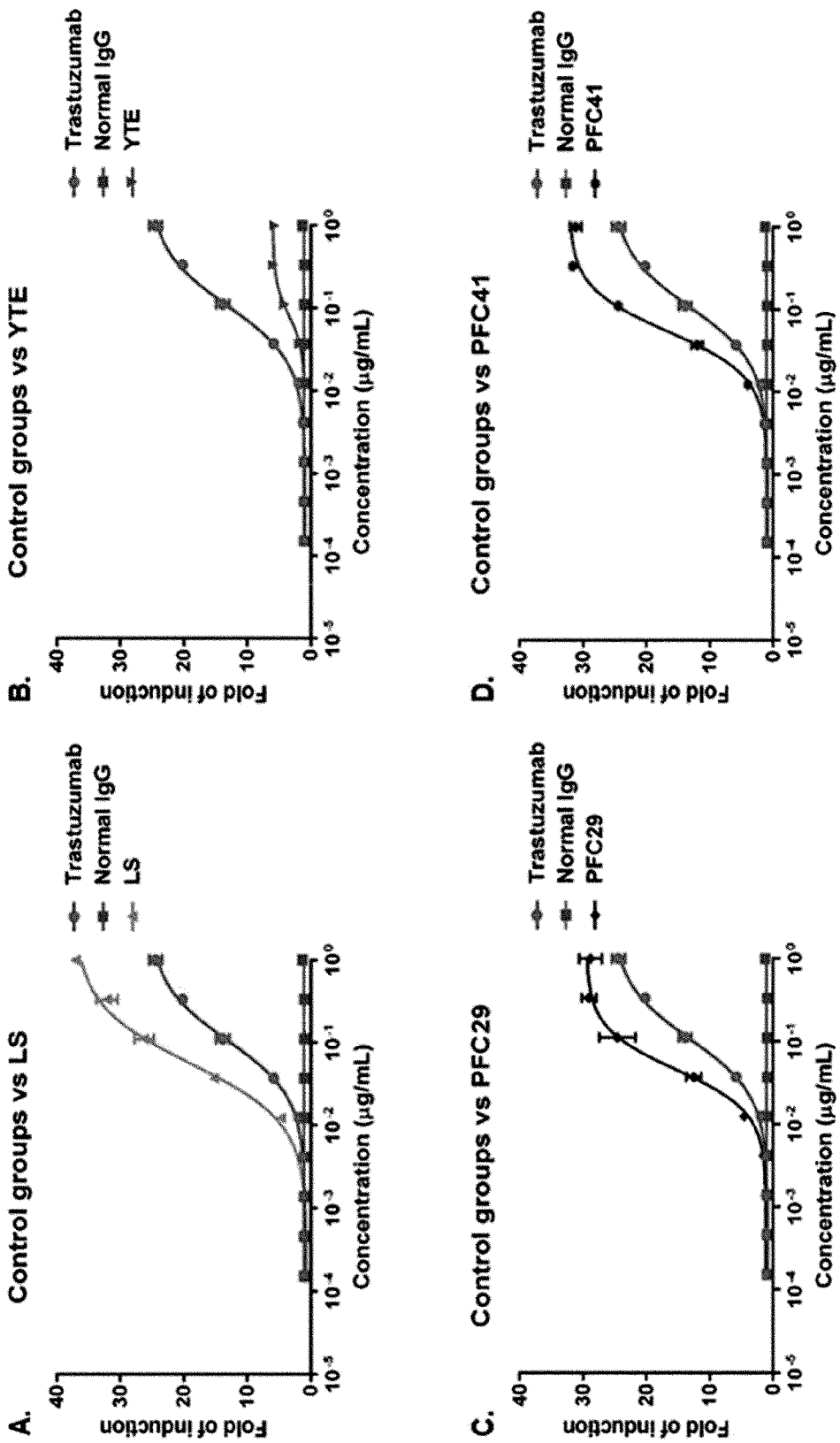
FIG. 17 compares the effector functions of trastuzumab Fc variants with those of normal IgG and trastuzumab as a control group (ADCC assay).
Figure 18:
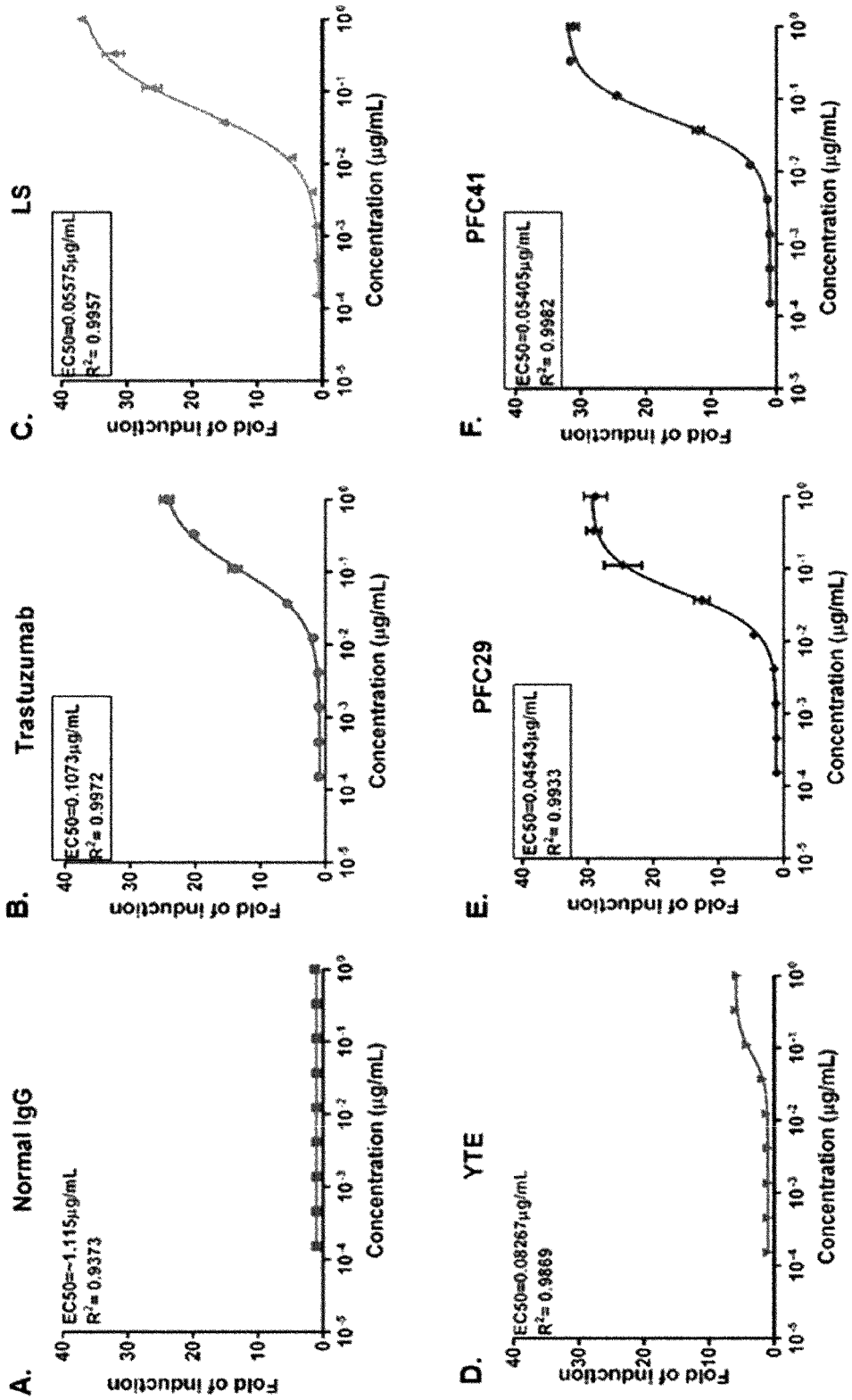
FIG. 18 compares the effector functions (ADCC) of trastuzumab Fc variants.

Example 12: Measurement of Binding Forces of the Fc Variants to FcγRs by ELISA In this example, the binding forces of the Fc variants to FcγRs were measured. Specifically, 50 μl of each of the IgG Fc variants diluted to 4 μg/ml with 0.05 M $Na_2CO_3$ (pH 9.6) was immobilized onto a flat-bottom polystyrene high-bind 96-well microplate (costar) at 4° C. for 16 h, blocked with 100 μl of 4% skim milk (GenomicBase) (in 0.05% PBST pH 7.4) at room temperature for 2 h, and washed four times with 180 μl of 0.05% PBST (pH 7.4). Thereafter, 50 μl of FcγRs serially diluted with 1% skim milk (in 0.05% PBST pH 7.4) was plated in each well and the reaction was carried out at room temperature for 1 h. After washing, an antibody reaction with 50 μl of anti-GST-HRP conjugate (GE Healthcare) was allowed to proceed at room temperature for 1 h. The plate was washed and developed with 50 μl of 1-Step Ultra TMB-ELISA Substrate Solution (Thermo Fisher Scientific). The reaction was quenched with 2 M $H_2SO_4$ (50 μl each). Then, the reaction product was analyzed using an epoch microplate spectrophotometer (BioTek). Each experiment was conducted in duplicate. FIG. 16 shows the binding forces of the Fc variants to FcγRs (FcγRI, FcγRIIa(H), FcγRIIa(R), FcγRIIb, FcγRIIIa(V), and FcγRIIIa(F)), which were measured by ELISA.

provided from the kit were dissolved in a thermostatic water bath at 37° C. for 2-3 min and 630 μl of the solution was mixed with 3.6 mL of ADCC assay buffer. 25 μl of the effector cells were plated in each well of the plate containing the target cells and the antibody dilution. The reaction was carried out in a C02 incubator at 37° C. for 6 h. After the lapse of a predetermined time, the plate was taken out of the incubator and placed at room temperature for 15 min. 75 μl of Bio-Glo™ Luciferase assay reagent was added to each well and the reaction was carried out at room temperature for 5 min. After completion of the reaction, the luminescence of each well was measured using a luminometer (Enspire multimode plate reader). The ADCC activity of each test antibody was determined by expressing the average of the experimental results as a fold induction, which was calculated by the following equation:

Fold induction=RLU(induced[1]−background[2])/RLU (no antibody control[3]−background)

induced[1]: RLU value acquired from the sample containing the target cells, the test antibody and the effector cells
background[2]: RLU value acquired from the ADCC assay buffer
no antibody control[3]: RLU value acquired from the sample containing the target cells and the effector cells only The ADCC activities of the trastuzumab Fc variants (LS, YTE, PFC29, and PFC41) for SKBR-3 were compared with that of trastuzumab (FIG. 17). As a result, the maximum ADCC activities of LS, PFc29, and PFc41 at their highest concentrations were ~1.5, ~1.18, and ~1.27-fold higher than that of trastuzumab as the positive control group, respectively. In contrast, the maximum ADCC activity of YTE at its highest concentration was ~4.2-fold lower than that of trastuzumab. In conclusion, the trastuzumab Fc variants PFc29 and PFc41 and the control variant LS achieved ADCC activities 1.18-1.5 times higher than that of the control trastuzumab. The EC50 values of the variants were measured. As shown in FIG. 18, the lower EC50 values of the Fc variant PFc29 (0.04543 μg/mL) and PFc41 (0.05405 μg/mL) than the control LS (0.05575 μg/mL) indicate that the efficacies of the Fc variants PFc29 and PFc41 were more stable.

Example 14: Measurement of Binding Forces of the Fc Variants to C1q by ELISA

Figure 19:
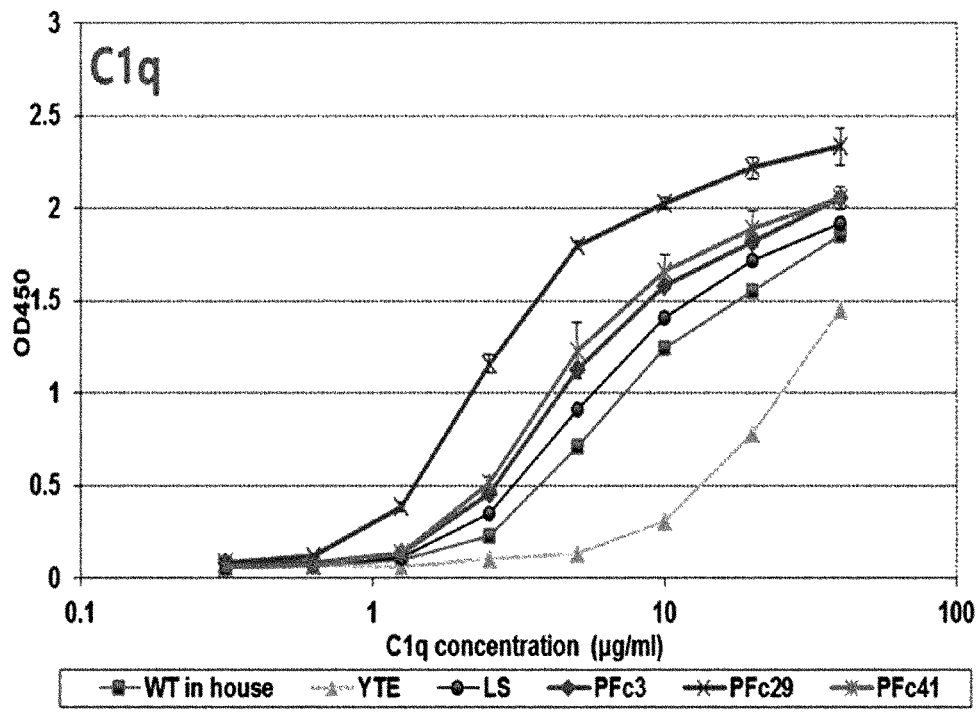
FIG. 19 shows binding forces of trastuzumab Fc variants to C1q, which were measured by ELISA.
Figure 19:
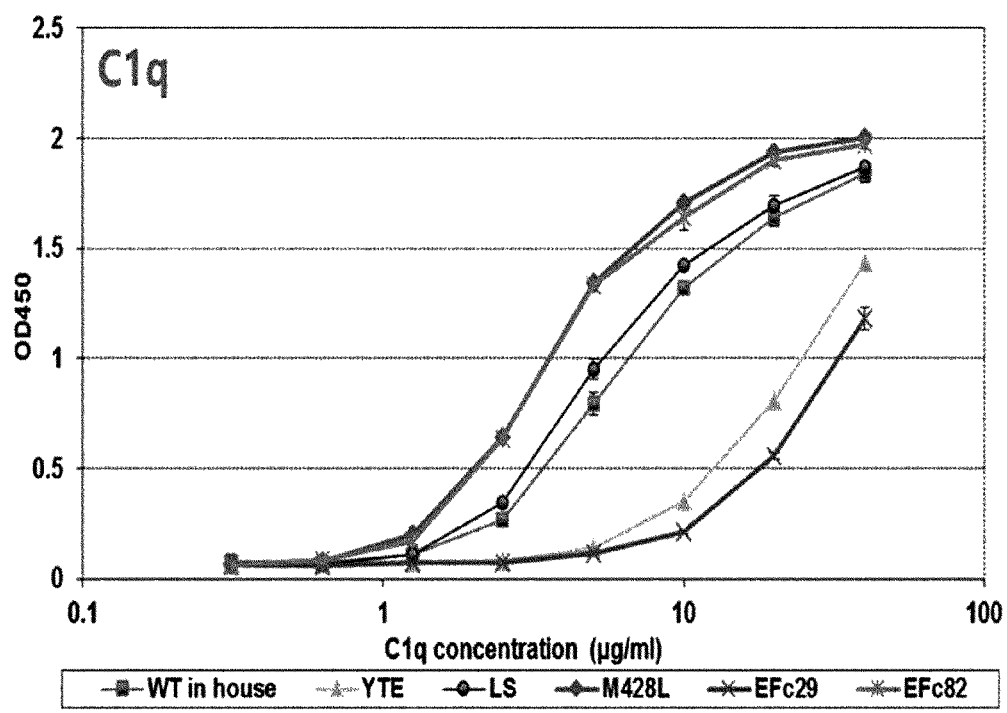

In this example, the binding forces of the Fc variants to C1q were measured. Specifically, 50 μl of each of the IgG Fc variants diluted to 4 μg/ml with 0.05 M $Na_2CO_3$ (pH 9.6) was immobilized onto a flat-bottom polystyrene high-bind 96-well microplate (costar) at 4° C. for 16 h, blocked with 100 μl of 4% skim milk (GenomicBase) (in 0.05% PBST pH 7.4) at room temperature for 2 h, and washed four times with 180 μl of 0.05% PBST (pH 7.4). Thereafter, 50 μl of Complement C1q Human (Millipore) serially diluted with 1% skim milk (in 0.05% PBST pH 7.4) was plated in each well and the reaction was carried out at room temperature for 1 h. After washing, an antibody reaction with 50 μl of anti-C1q-HRP conjugate (Invitrogen) was allowed to proceed at room temperature for 1 h. The plate was washed and developed with 50 μl of 1-Step Ultra TMB-ELISA Substrate Solution (Thermo Fisher Scientific). The reaction was quenched with 2 M $H_2SO_4$ (50 μl each). Then, the reaction product was analyzed using an epoch microplate spectrophotometer (BioTek). As a result of the analysis, the binding force of the sorted PFc29 to C1q was higher than those of conventional LS and YTE (FIG. 19).

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

The invention claimed is:

1. A polypeptide comprising a human antibody with Fc variant wherein the Fc variant consists of, as amino acid substitutions, M428L and Q311R or M428L and L309G according to the Kabat EU numbering system in the Fc domain of the wild-type human antibody, and wherein the Fc variant has an increased half-life of the human antibody compared to the wild type.

2. The polypeptide according to claim 1, wherein the antibody is an IgG antibody.

3. The antibody according to claim 1, wherein the antibody is a monoclonal antibody, a bispecific antibody, an antibody conjugate, or a human antibody.

4. A composition comprising the polypeptide according to claim 1, an antibody comprising the polypeptide, a nucleic acid molecule comprising the polypeptide or vector comprising the nucleic acid molecule.

5. The composition according to claim 4, wherein the composition increases the blood half-life of the antibody for therapy in vivo.

6. The composition according to claim 4, wherein the composition is a pharmaceutical composition for treating cancer.

7. The composition according to claim 6, wherein the antibody recognizes a cancer antigen.

* * * * *

SEQUENCE LISTING

```
<160> NUMBER OF SEQ ID NOS: 37

<210> SEQ ID NO 1
<211> LENGTH: 20
<212> TYPE: DNA
<213> ORGANISM: Artificial Sequence
<220> FEATURE:
<223> OTHER INFORMATION: pMopac12-seq-Fw

<400> SEQUENCE: 1
ccaggcttta cactttatgc                                              20

<210> SEQ ID NO 2
<211> LENGTH: 44
<212> TYPE: DNA
<213> ORGANISM: Artificial Sequence
<220> FEATURE:
<223> OTHER INFORMATION: Fc-M252-1-Rv

<400> SEQUENCE: 2
cctcaggggt ccgggagatg wagagggtgt ccttgggttt tggg                   44

<210> SEQ ID NO 3
<211> LENGTH: 44
<212> TYPE: DNA
<213> ORGANISM: Artificial Sequence
<220> FEATURE:
<223> OTHER INFORMATION: Fc-M252-2-Rv
<220> FEATURE:
<221> NAME/KEY: variation
<222> LOCATION: (21)
<223> OTHER INFORMATION: n is a, g, c or t.

<400> SEQUENCE: 3
cctcaggggt ccgggagatk nbgagggtgt ccttgggttt tggg                   44

<210> SEQ ID NO 4
<211> LENGTH: 44
<212> TYPE: DNA
<213> ORGANISM: Artificial Sequence
```

```
<220> FEATURE:
<223> OTHER INFORMATION: Fc-M252-3-Rv

<400> SEQUENCE: 4
cctcaggggt ccgggagatc cagagggtgt ccttgggttt tggg          44

<210> SEQ ID NO 5
<211> LENGTH: 19
<212> TYPE: DNA
<213> ORGANISM: Artificial Sequence
<220> FEATURE:
<223> OTHER INFORMATION: Fc-M428-Fw

<400> SEQUENCE: 5
atctcccgga cccctgagg                                       19

<210> SEQ ID NO 6
<211> LENGTH: 50
<212> TYPE: DNA
<213> ORGANISM: Artificial Sequence
<220> FEATURE:
<223> OTHER INFORMATION: Fc-M428-1-Rv

<400> SEQUENCE: 6
gtagtggttg tgcagagcct catggwacac ggagcatgag aagacgttcc     50

<210> SEQ ID NO 7
<211> LENGTH: 50
<212> TYPE: DNA
<213> ORGANISM: Artificial Sequence
<220> FEATURE:
<223> OTHER INFORMATION: Fc-M428-2-Rv
<220> FEATURE:
<221> NAME/KEY: variation
<222> LOCATION: (26)
<223> OTHER INFORMATION: n is a, g, c or t.

<400> SEQUENCE: 7
gtagtggttg tgcagagcct catgknbcac ggagcatgag aagacgttcc     50

<210> SEQ ID NO 8
<211> LENGTH: 50
<212> TYPE: DNA
<213> ORGANISM: Artificial Sequence
<220> FEATURE:
<223> OTHER INFORMATION: Fc-M428-3-Rv

<400> SEQUENCE: 8
gtagtggttg tgcagagcct catgccacac ggagcatgag aagacgttcc     50

<210> SEQ ID NO 9
<211> LENGTH: 24
<212> TYPE: DNA
<213> ORGANISM: Artificial Sequence
<220> FEATURE:
<223> OTHER INFORMATION: Fc-M428-frg3-Fw

<400> SEQUENCE: 9
catgaggctc tgcacaacca ctac                                 24

<210> SEQ ID NO 10
<211> LENGTH: 19
<212> TYPE: DNA
<213> ORGANISM: Artificial Sequence
<220> FEATURE:
<223> OTHER INFORMATION: pMopac12-seq-Rv
```

<400> SEQUENCE: 10
ctgcccatgt tgacgattg                                           19

<210> SEQ ID NO 11
<211> LENGTH: 22
<212> TYPE: DNA
<213> ORGANISM: Artificial Sequence
<220> FEATURE:
<223> OTHER INFORMATION: Fc-Sub#0-Rv

<400> SEQUENCE: 11
gtccttgggt tttgggggga ag                                       22

<210> SEQ ID NO 12
<211> LENGTH: 59
<212> TYPE: DNA
<213> ORGANISM: Artificial Sequence
<220> FEATURE:
<223> OTHER INFORMATION: Fc-Sub#1-1-Fw
<220> FEATURE:
<221> NAME/KEY: variation
<222> LOCATION: (23)..(24)
<223> OTHER INFORMATION: n is a, g, c or t.

<400> SEQUENCE: 12 cttccccccca aaacccaagg acnnkctcat gatctcccgg acccctgagg tcacatgcg    59

<210> SEQ ID NO 13
<211> LENGTH: 59
<212> TYPE: DNA
<213> ORGANISM: Artificial Sequence
<220> FEATURE:
<223> OTHER INFORMATION: Fc-Sub#1-2-Fw
<220> FEATURE:
<221> NAME/KEY: variation
<222> LOCATION: (26)..(27)
<223> OTHER INFORMATION: n is a, g, c or t.

<400> SEQUENCE: 13 cttccccccca aaacccaagg acaccnnkat gatctcccgg acccctgagg tcacatgcg    59

<210> SEQ ID NO 14
<211> LENGTH: 59
<212> TYPE: DNA
<213> ORGANISM: Artificial Sequence
<220> FEATURE:
<223> OTHER INFORMATION: Fc-Sub#1-3-Fw
<220> FEATURE:
<221> NAME/KEY: variation
<222> LOCATION: (32)..(33)
<223> OTHER INFORMATION: n is a, g, c or t.

<400> SEQUENCE: 14 cttccccccca aaacccaagg acaccctcat gnnktcccgg acccctgagg tcacatgcg    59

<210> SEQ ID NO 15
<211> LENGTH: 59
<212> TYPE: DNA
<213> ORGANISM: Artificial Sequence
<220> FEATURE:
<223> OTHER INFORMATION: Fc-Sub#1-4-Fw
<220> FEATURE:
<221> NAME/KEY: variation
<222> LOCATION: (35)..(36)
<223> OTHER INFORMATION: n is a, g, c or t.

<400> SEQUENCE: 15 cttccccccca aaacccaagg acaccctcat gatcnnkcgg acccctgagg tcacatgcg    59

```
<210> SEQ ID NO 16
<211> LENGTH: 59
<212> TYPE: DNA
<213> ORGANISM: Artificial Sequence
<220> FEATURE:
<223> OTHER INFORMATION: Fc-Sub#1-5-Fw
<220> FEATURE:
<221> NAME/KEY: variation
<222> LOCATION: (38)..(39)
<223> OTHER INFORMATION: n is a, g, c or t.

<400> SEQUENCE: 16
cttcccccca aaacccaagg acaccctcat gatctccnnk acccctgagg tcacatgcg      59

<210> SEQ ID NO 17
<211> LENGTH: 19
<212> TYPE: DNA
<213> ORGANISM: Artificial Sequence
<220> FEATURE:
<223> OTHER INFORMATION: Fc-Sub#1-Rv

<400> SEQUENCE: 17
gacggtgagg acgctgacc                                                  19

<210> SEQ ID NO 18
<211> LENGTH: 62
<212> TYPE: DNA
<213> ORGANISM: Artificial Sequence
<220> FEATURE:
<223> OTHER INFORMATION: Fc-Sub#2-1-Fw
<220> FEATURE:
<221> NAME/KEY: variation
<222> LOCATION: (20)..(21)
<223> OTHER INFORMATION: n is a, g, c or t.

<400> SEQUENCE: 18
ggtcagcgtc ctcaccgtcn nkcaccagga ctggctgaat ggcaaggagt acaagtgcaa     60
gg                                                                    62

<210> SEQ ID NO 19
<211> LENGTH: 62
<212> TYPE: DNA
<213> ORGANISM: Artificial Sequence
<220> FEATURE:
<223> OTHER INFORMATION: Fc-Sub#2-2-Fw
<220> FEATURE:
<221> NAME/KEY: variation
<222> LOCATION: (26)..(27)
<223> OTHER INFORMATION: n is a, g, c or t.

<400> SEQUENCE: 19
ggtcagcgtc ctcaccgtcc tgcacnnkga ctggctgaat ggcaaggagt acaagtgcaa     60
gg                                                                    62

<210> SEQ ID NO 20
<211> LENGTH: 62
<212> TYPE: DNA
<213> ORGANISM: Artificial Sequence
<220> FEATURE:
<223> OTHER INFORMATION: Fc-Sub#2-3-Fw
<220> FEATURE:
<221> NAME/KEY: variation
<222> LOCATION: (35)..(36)
<223> OTHER INFORMATION: n is a, g, c or t.

<400> SEQUENCE: 20
```

```
ggtcagcgtc ctcaccgtcc tgcaccagga ctggnnkaat ggcaaggagt acaagtgcaa    60
gg                                                                   62
```

<210> SEQ ID NO 21
<211> LENGTH: 23
<212> TYPE: DNA
<213> ORGANISM: Artificial Sequence
<220> FEATURE:
<223> OTHER INFORMATION: Fc-Sub#2-Rv

<400> SEQUENCE: 21

```
cacggagcat gagaagacgt tcc                                            23
```

<210> SEQ ID NO 22
<211> LENGTH: 71
<212> TYPE: DNA
<213> ORGANISM: Artificial Sequence
<220> FEATURE:
<223> OTHER INFORMATION: Fc-Sub#3-1-Fw
<220> FEATURE:
<221> NAME/KEY: variation
<222> LOCATION: (30)..(31)
<223> OTHER INFORMATION: n is a, g, c or t.

<400> SEQUENCE: 22

```
ggaacgtctt ctcatgctcc gtgctgcatn nkgctctgca caaccactac acgcagaaga    60
gcctctccct g                                                         71
```

<210> SEQ ID NO 23
<211> LENGTH: 71
<212> TYPE: DNA
<213> ORGANISM: Artificial Sequence
<220> FEATURE:
<223> OTHER INFORMATION: Fc-Sub#3-2-Fw
<220> FEATURE:
<221> NAME/KEY: variation
<222> LOCATION: (30)..(31)
<223> OTHER INFORMATION: n is a, g, c or t.

<400> SEQUENCE: 23

```
ggaacgtctt ctcatgctcc gtgctgcatn nkgctctgca caaccactac acgcagaaga    60
gcctctccct g                                                         71
```

<210> SEQ ID NO 24
<211> LENGTH: 71
<212> TYPE: DNA
<213> ORGANISM: Artificial Sequence
<220> FEATURE:
<223> OTHER INFORMATION: Fc-Sub#3-3-Fw
<220> FEATURE:
<221> NAME/KEY: variation
<222> LOCATION: (42)..(43)
<223> OTHER INFORMATION: n is a, g, c or t.

<400> SEQUENCE: 24

```
ggaacgtctt ctcatgctcc gtgctgcatg aggctctgca cnnkcactac acgcagaaga    60
gcctctccct g                                                         71
```

<210> SEQ ID NO 25
<211> LENGTH: 71
<212> TYPE: DNA
<213> ORGANISM: Artificial Sequence
<220> FEATURE:
<223> OTHER INFORMATION: Fc-Sub#3-4-Fw
<220> FEATURE:
<221> NAME/KEY: variation

```
<222> LOCATION: (48)..(49)
<223> OTHER INFORMATION: n is a, g, c or t.

<400> SEQUENCE: 25
ggaacgtctt ctcatgctcc gtgctgcatg aggctctgca caaccacnnk acgcagaaga      60
gcctctccct g                                                          71

<210> SEQ ID NO 26
<211> LENGTH: 16
<212> TYPE: DNA
<213> ORGANISM: Artificial Sequence
<220> FEATURE:
<223> OTHER INFORMATION: ep-Fc-Fw

<400> SEQUENCE: 26
ccagccggcc atggcg                                                     16

<210> SEQ ID NO 27
<211> LENGTH: 21
<212> TYPE: DNA
<213> ORGANISM: Artificial Sequence
<220> FEATURE:
<223> OTHER INFORMATION: ep-Fc-Rv

<400> SEQUENCE: 27
gaattcggcc cccgaggccc c                                               21

<210> SEQ ID NO 28
<211> LENGTH: 227
<212> TYPE: PRT
<213> ORGANISM: Homo sapiens

<400> SEQUENCE: 28
```

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 29
<211> LENGTH: 681
<212> TYPE: DNA
<213> ORGANISM: Homo sapiens

<400> SEQUENCE: 29
gacaaaactc acacatgccc accgtgccca gcacctgaac tcctgggggg accgtcagtc    60
ttcctcttcc cccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc aagacaaag ccgcgggagg agcagtacaa cagcacgtac   240
cgtgtggtca gcgtcctcac cgtcctgcac caggactggc tgaatggcaa ggagtacaag   300
tgcaaggtct ccaacaaagc cctcccagcc cccatcgaga aaaccatctc aaagccaaa   360 gggcagcccc gagaaccaca ggtgtacacc ctgcccccat cccgggatga gctgaccaag   420
aaccaggtca gcctgacctg cctggtcaaa ggcttctatc ccagcgacat cgccgtggag   480
tgggagagca tgggcagcc ggagaacaac tacaagacca cacctcccgt gctggactcc   540
gacggctcct tcttcctcta cagcaagctc accgtggaca agagcaggtg gcagcagggg   600
aacgtcttct catgctccgt gatgcatgag gctctgcaca accactacac gcagaagagc   660
ctctccctgt ccccgggtaa a                                              681

<210> SEQ ID NO 30
<211> LENGTH: 227
<212> TYPE: PRT
<213> ORGANISM: Artificial Sequence
<220> FEATURE:
<223> OTHER INFORMATION: PFc 3

<400> SEQUENCE: 30

Asp Lys Thr His Thr Cys Pro Leu Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Arg His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Ser His Tyr Thr Gln Lys Ser Leu Ser Leu Ser
    210                 215                 220

Pro Gly Lys
225

<210> SEQ ID NO 31
<211> LENGTH: 227
<212> TYPE: PRT
<213> ORGANISM: Artificial Sequence
<220> FEATURE:
<223> OTHER INFORMATION: PFc 29

<400> SEQUENCE: 31

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Arg Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 32
<211> LENGTH: 227
<212> TYPE: PRT
<213> ORGANISM: Artificial Sequence
<220> FEATURE:
<223> OTHER INFORMATION: PFc 41

<400> SEQUENCE: 32
```

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Gly His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
            195                 200                 205

His Glu Ala Leu His Asn His Tyr Thr Gln Lys Ser Leu Ser Leu Ser
210                 215                 220

Pro Gly Lys
225

<210> SEQ ID NO 33
<211> LENGTH: 227
<212> TYPE: PRT
<213> ORGANISM: Artificial Sequence
<220> FEATURE:
<223> OTHER INFORMATION: EFc 6

<400> SEQUENCE: 33

Asp Lys Thr His Thr Cys Pro Leu Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Met Asp Val Ser His
            35                  40                  45

Glu Asp Pro Glu Val Lys Phe Asn Trp Tyr Val Asp Gly Val Glu Val
50                      55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125
```

```
Tyr Thr Leu Pro Pro Ser Arg Asp Glu Leu Thr Lys Asn Gln Val Ser
        130                 135                 140

Leu Thr Cys Gln Val Lys Gly Phe Tyr Pro Ser Asp Ile Ala Val Glu
145                 150                 155                 160

Trp Glu Ser Asn Gly Gln Pro Asp Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Asp Phe Ser Cys Ser Val Leu
            195                 200                 205

His Glu Ala Leu His Asn His Tyr Thr Gln Lys Ser Leu Ser Leu Ser
        210                 215                 220

Ser Gly Lys
225

<210> SEQ ID NO 34
<211> LENGTH: 227
<212> TYPE: PRT
<213> ORGANISM: Artificial Sequence
<220> FEATURE:
<223> OTHER INFORMATION: EFc 29

<400> SEQUENCE: 34

Asp Lys Thr His Thr Cys Pro Leu Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Leu Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Ala Lys Asn Gln Val Gly
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
            195                 200                 205

His Glu Ala Leu His Asn His Tyr Thr Gln Lys Ser Leu Ser Leu Ser
        210                 215                 220

Pro Gly Lys
225

<210> SEQ ID NO 35
```

```
<211> LENGTH: 227
<212> TYPE: PRT
<213> ORGANISM: Artificial Sequence
<220> FEATURE:
<223> OTHER INFORMATION: EFc 41

<400> SEQUENCE: 35

Asp Lys Thr His Thr Cys Pro Leu Cys Pro Ala Pro Glu Phe Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Leu Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Asp Asn Asn Tyr Lys Thr Ala Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
    210                 215                 220

Pro Gly Lys
225

<210> SEQ ID NO 36
<211> LENGTH: 227
<212> TYPE: PRT
<213> ORGANISM: Artificial Sequence
<220> FEATURE:
<223> OTHER INFORMATION: EFc 82

<400> SEQUENCE: 36

Asp Lys Thr His Thr Cys Pro Pro Cys Gln Ala Pro Glu Leu Leu Gly
1               5                   10                  15

Gly Pro Ser Val Phe Leu Tyr Pro Pro Glu Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
```

```
                     85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Ser Gln Val Ser
        130                 135                 140

Leu Thr Cys Leu Val Lys Gly Phe Tyr Pro Ser Asp Ile Ala Val Glu
145                 150                 155                 160

Trp Glu Ser Ile Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Leu
            195                 200                 205

His Glu Ala Leu His Asn His Tyr Thr Gln Lys Ser Leu Ser Leu Ser
        210                 215                 220

Pro Gly Lys
225

<210> SEQ ID NO 37
<211> LENGTH: 227
<212> TYPE: PRT
<213> ORGANISM: Artificial Sequence
<220> FEATURE:
<223> OTHER INFORMATION: EFc 88

<400> SEQUENCE: 37

Asp Lys Thr His Thr Cys Pro Pro Cys Ser Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Leu Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Met Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Ile Leu Tyr Ser Lys Leu Thr Val
            180                 185                 190
```

```
Asp Lys Ser Arg Trp Gln Gln Gly Asn Val Phe Ser Cys Ser Val Leu
        195                 200                 205

His Glu Ala Leu His Asn His Tyr Thr Gln Lys Ser Leu Ser Leu Ser
        210                 215                 220

Pro Gly Lys
225
```